(12) United States Patent
Wolf, II

(10) Patent No.: US 8,500,738 B2
(45) Date of Patent: Aug. 6, 2013

(54) ELECTROMAGNETIC APPARATUS AND METHOD FOR NERVE LOCALIZATION DURING SPINAL SURGERY

(76) Inventor: Erich Wolf, II, Lake Charles, LA (US)

( * ) Notice: Subject to any disclaimer, the term of this patent is extended or adjusted under 35 U.S.C. 154(b) by 15 days.

(21) Appl. No.: 13/200,607

(22) Filed: Sep. 24, 2011

(65) Prior Publication Data

US 2012/0022394 A1 Jan. 26, 2012

Related U.S. Application Data

(63) Continuation of application No. 11/897,169, filed on Aug. 28, 2007, now Pat. No. 8,052,688.

(60) Provisional application No. 60/849,858, filed on Oct. 6, 2006.

(51) Int. Cl.
*A61B 17/16* (2006.01)

(52) U.S. Cl.
USPC ............................................. 606/79; 606/130

(58) Field of Classification Search
USPC .................. 606/79, 80, 130; 600/554
See application file for complete search history.

(56) References Cited

U.S. PATENT DOCUMENTS

| 6,013,083 | A | | 1/2000 | Bennett |
| 6,155,966 | A | * | 12/2000 | Parker ............................. 600/13 |
| 6,285,902 | B1 | | 9/2001 | Kienzle, III et al. |
| 6,478,802 | B2 | | 11/2002 | Kienzle, III et al. |
| 6,796,985 | B2 | | 9/2004 | Bolger et al. |
| 2002/0161372 | A1 | * | 10/2002 | Bolger et al. ................... 606/80 |
| 2006/0025703 | A1 | | 2/2006 | Miles et al. |

FOREIGN PATENT DOCUMENTS

WO WO 03/070317 A1 2/2003

OTHER PUBLICATIONS

Erich W. Wolf II; Electrophysiological Search for Magnetic Field Influence on Ion Channel Gating in N1E-115 Neuroblastoma Cells; 1994, Doctoral Thesis, Tulane University.
Kevin T Foley, M.D., et al.; Percutaneous pedicle screw fixation of the lumbar spine; Apr., 2001; Neuorsurg Focus, vol. 10, pp. 1-8, Dept. of Neurosurgery, Univ. of Tennessee.

* cited by examiner

*Primary Examiner* — Kevin T Truong
*Assistant Examiner* — Christian Sevilla
(74) *Attorney, Agent, or Firm* — Schultz & Associates, P.C.

(57) ABSTRACT

An electromagnetic pedicle awl utilizes a tightly focused time-varying magnetic flux to create a localized electromotive force (EMF) near the tip. The localized EMF creates localized eddy currents in nearby nerves which excite ionic nerve channels, the excitation being detected by an electromyographic recording device. The awl only excites nerves directly in front of and directly to the side of the tip. The awl is comprised of a tapered awl or drill tip in combination with a solid core surrounded by a solenoid. A pulsed electric current source drives the solenoid to create a time-varying magnetic field in the vicinity of the tapered tip. The awl or drill tip may be stationary with respect to the solenoid or it may rotate. The awl in combination with an EMG detector connected to a patient is sensitive to the pedicle hole position with respect to adjacent nerves and reduces false placement failure.

17 Claims, 16 Drawing Sheets

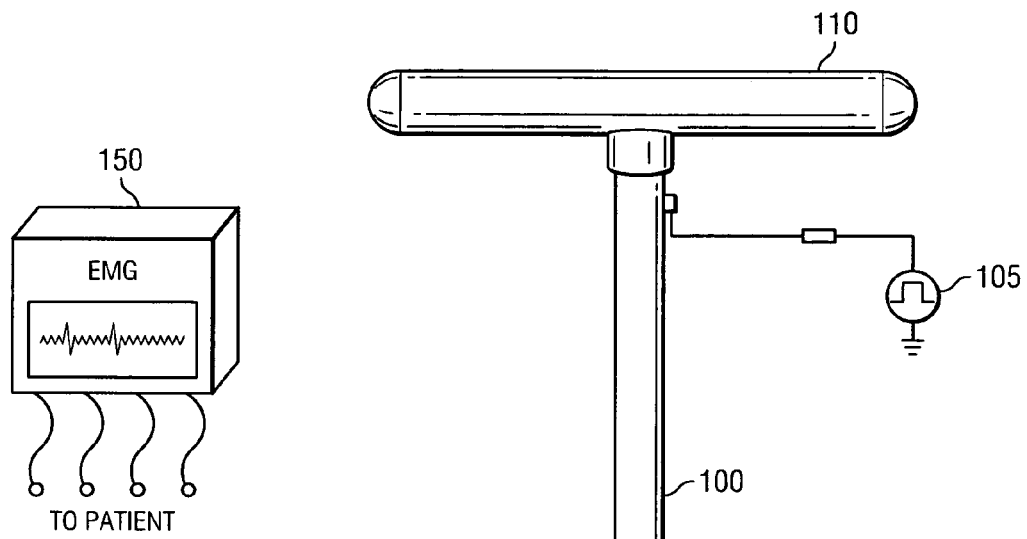
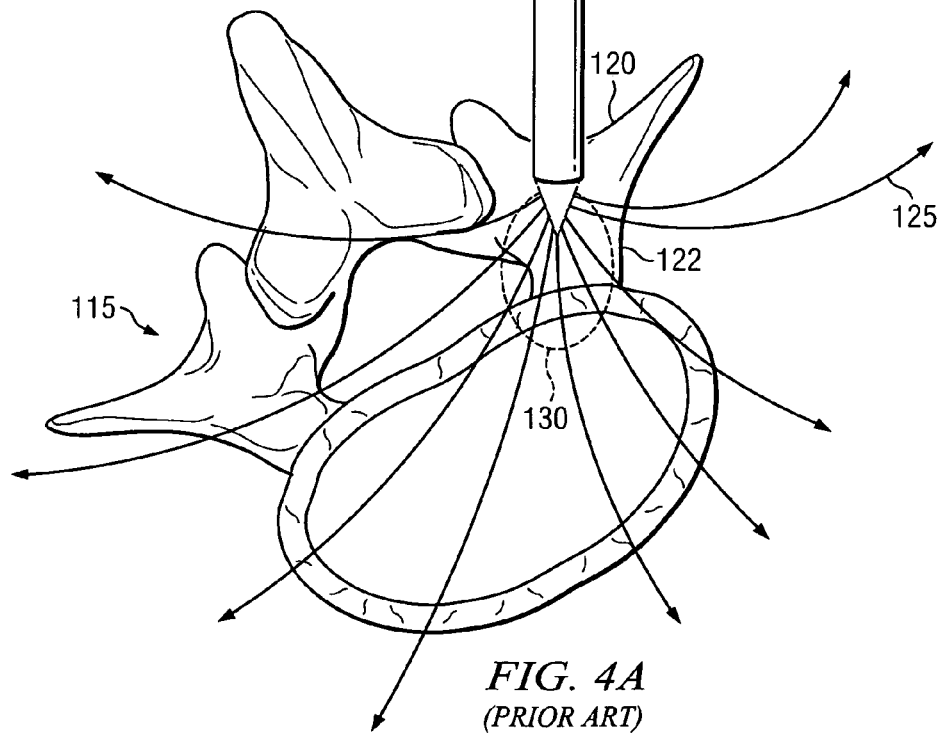
FIG. 4B
FIG. 4A
(PRIOR ART)

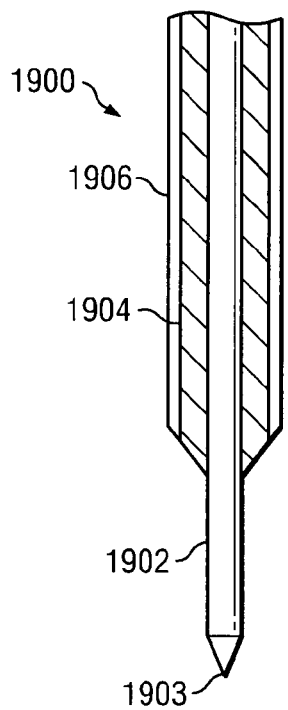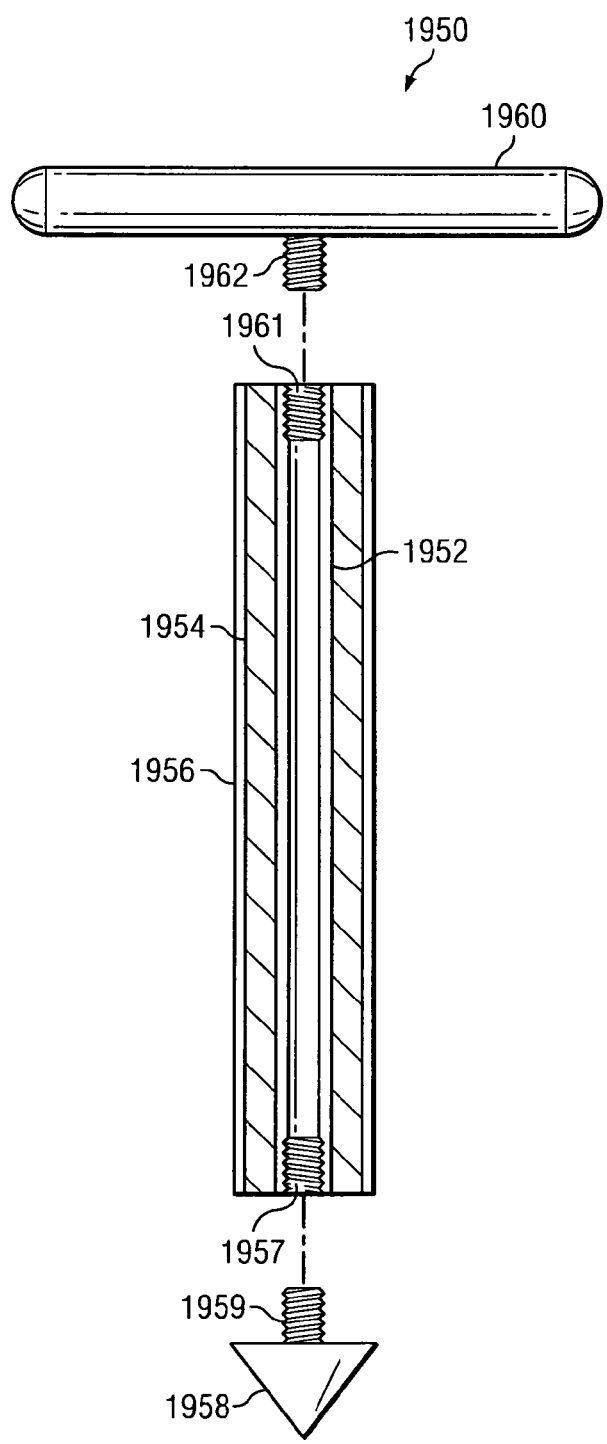
FIG. 19
FIG. 20

ELECTROMAGNETIC APPARATUS AND METHOD FOR NERVE LOCALIZATION DURING SPINAL SURGERY

CROSS-REFERENCE TO RELATED APPLICATION

This application is a Continuation claiming priority benefit from U.S. patent application Ser. No. 11/897,169 entitled "Electromagnetic Apparatus and Method for Nerve Localization During Spinal Surgery" which was filed Aug. 28, 2007 now U.S. Pat. No. 8,052,688 which claims priority to U.S. Provisional Application Ser. No. 60/849,858 entitled "Electromagnetic Pedicle Screw Placement Apparatus and Method" which was filed on Oct. 6, 2006.

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD OF INVENTION

The present invention relates generally to the avoidance of nervous system injury during surgery for correction of spinal column injuries, degeneration and deformities in the fields of neurosurgery and orthopedics. More specifically, the invention is used for the placement of medical instrumentation apparatus into and between spinal vertebrae.

BACKGROUND OF THE INVENTION

Spinal conditions such as degenerative disc disease or spondylolisthesis can cause signs and symptoms that include back or lower extremity pain, muscle spasms, weakness, dysfunction of bowel and/or bladder, and gait disturbance.

To correct these and other similar conditions of vertebral dislocation, the only effective long-term curative treatment may be achieved by fusion of the affected vertebra to its adjacent neighbor. Vertebral fusion is generally augmented by instrumentation, or fixing apparatus, to and between vertebrae. Transpedicular fixation is a particularly important process in the treatment of spinal conditions that require vertebral fusion. In addition to the stabilization and correction of spondylolisthesis, other spinal conditions may be treated by transpedicular fixation: stabilization of fractures, correction of spinal deformities (scoliosis, kyphosis), stabilization and correction of degenerative spinal lesions, reconstruction after tumor resection, and secondary spinal surgery.

In FIG. 1, a drawing of the human spine shows that the spinal column 1 is comprised of a number of vertebrae, categorized into four sections or types: the lumbar vertebrae 2, the thoracic vertebrae 3, the cervical vertebrae 4 and the sacral vertebrae 5. Starting at the top of the spinal column 1, the cervical vertebrae 4 are labeled $1^{st}$ cervical vertebra (C1) through $7^{th}$ cervical vertebra (C7). Just below the $7^{th}$ cervical vertebra is the first of twelve thoracic vertebrae 3 labeled $1^{st}$ thoracic vertebra (T1) through $12^{th}$ thoracic vertebra (T12). Just below the $12^{th}$ thoracic vertebrae 3, are five lumbar vertebrae 2 labeled $1^{st}$ lumbar vertebra (L1) through $5^{th}$ lumbar vertebra (L5), the $5^{th}$ lumbar vertebra being attached to the sacral vertebrae 5 (S1 to S5), the sacral vertebrae 5 being naturally fused together in the adult.

Spinal fusion surgery typically involves the corrective fusion of lumbar vertebrae 2, of which a representative transverse drawing of such a vertebra is shown in FIG. 2. Representative lumbar vertebra 10 has a number of notable features which are in general shared with the thoracic vertebrae 3 and cervical vertebrae 4, although the feature thicknesses and shapes may alter between the various types of vertebrae. The thick oval segment of bone forming the anterior aspect of the vertebra 10 is the vertebral body 12. Vertebral body 12 is attached to a bony vertebral arch 13 through which the neural elements run. Vertebral arch 13, forming the posterior of vertebra 10, is comprised of two pedicles 14, which are short stout processes that extend from the sides of vertebral body 12, and two laminae 15, the broad flat plates that project from pedicles 14 and join in a triangle to form a hollow archway, the vertebral foramen 16 or spinal canal. The spinous process 17 protrudes from the junction of laminae 15: these are the ridges that can be felt through the skin along the back of the spine. Transverse processes 18 project from the junction of pedicles 14 and laminae 15. The structures of the vertebral arch protect the spinal cord and/or spinal nerves that run through the spinal canal.

The pedicles of typical lumbar vertebra increase in sagittal width from 9 mm to up to 18 mm at L5 (lowest lumbar vertebra). They increase in angulation in the axial plane from 10 degrees at L1 to 30 degrees by L5. Pedicles of the thoracic and cervical vertebra are typically smaller—as small as 4 mm in an adult. Pedicle widths in adolescents are proportionally smaller. The pedicles exhibit good mechanical strength in comparison to the other vertebral features.

Pedicles are used as a portal of entrance into the vertebral body for fixation with pedicle screws for placement of stabilizing rods or plates for fusion as shown in FIGS. 3a and 3b. Pedicles are used due to their strength, size and proximity to ease of entrance through the posterior side of the human body. In FIG. 3a, a transverse view of vertebra 10 is shown including pedicular holes 25 are drilled and tapped with pedicular screws 20 inserted into the vertebral body 12 through pedicles 14.

Typical pedicle screws are made of titanium alloy, are MRI compatible, and are highly resistant to corrosion and fatigue. Pedicle screws have length ranges from 30 mm to 60 mm. The threaded (major) diameter ranges from 4.5 mm to 8.5 mm.

The transpedicular fixation process is accomplished by placing pedicle screws into the pedicular region of adjacent vertebrae, as in FIG. 3a, and attaching rods between the pedicle screws to stabilize the vertebrae with respect to each other. In FIG. 3b, a second vertebral structure, in this case a sacral vertebrae S1 is shown to be connected to L5 vertebra through a set of pedicle screws 23 inserted into L5, a set of pedicle screws 21 inserted into S1; the pedicle screws 23 and 21 being interconnected by a pair of rods 22. Rods 22 may be further connected to each other by a transverse rod 24. The transpedicular fixation is formed by pedicle screws 23, pedicle screws 21, rods 22 and transverse rod 24 which fixes the vertebra L5 and S1 with respect to each other, thereby allowing the vertebrae to fuse in the healing process. If not placed properly, the pedicle screws 23 (or pedicle screws 21) may breach the vertebral walls thereby leading to nerve root damage or pressure on the spinal cord. The mechanical integrity of the screw placement must also be sufficient to support the rod structures and remain intact under mechanical stress. The present invention is an apparatus and method that significantly improves the placement of pedicle holes (and screws)

so that vertebral walls are not breached and also promotes mechanical integrity and avoidance of neurological injury.

The method of placement of pedicle screws and fixtures in the prior art is typically done under open surgical operation where the patient's spine is exposed. More recently, percutaneous placement of pedicle screws and fixtures has become more commonplace, causing less tissue damage and allowing for more rapid healing. During each prior art method, a pilot hole, using a pedicle awl or drill, is carefully made through each pedicle and into the vertebral body. The hole is threaded and a pedicle screw inserted.

The position and angle of the pilot hole is crucial to a successful pedicle screw placement and can be difficult to achieve, especially in percutaneous operations. If the pilot hole breaches the pedicle wall, spinal nerve damage may occur accompanied by chronic pain in the patient. Worse yet, if the pedicle wall is breached medially in the cervical or thoracic spine, permanent spinal cord damage may result. Also, a breach will typically weaken the mechanical integrity of the pedicle screw fixture.

In the prior art, the ability to accurately judge the integrity of the pedicle is generally limited to post-operative observation. For example, pedicle screw misplacements are usually detected only when pain or neurological deficit is reported by the patent. Corrective surgery to reposition the malpositioned pedicle screw is expensive, carries inherent medical risks, and may not reverse the neurological deficit or pain.

Radiographic imaging and computer-assisted methods have been developed in the prior art to increase the probability of success in the operative process. For example, fluoroscopic imaging, essential to percutaneous pedicle screw placement, is used to take lateral and anterior-posterior images of the vertebrae and to guide wire placement. After guide wires have been inserted through the pedicle and into the vertebral body, a pilot hole is made using a cannulated pedicle awl. But placement errors still occur. While flouroscopic-assisted pedicle screw guidance decreases the risk of misplacement such equipment is expensive and is not universally available. Hence the methods developed in the prior art have not been entirely successful.

Referring to FIGS. 4a and 4b, it is known in the prior art to stimulate and detect electromyographic (EMG) signals generated from nerve roots that course along the outer surface of the pedicles. In such a prior art method an electrostatic pedicle awl 100 is charged with a current source 105. The current supplied from the current source creates an electric field 125 near the tip of the electrostatic awl which in turn causes charge migrations in nerve ion channels in the vicinity of the tip area shown as the region of nerve excitation 130.

In use, the electrostatic pedicle awl 100 of the prior art is initially positioned by sight or by fluoroscopic imaging onto a pedicle 120 of vertebra 115 and then rotated using a removable handle 110 and lightly tapped with a hammer (not shown) to create the pilot hole. An EMG 150 is taken of muscles that respond to specific nerves in the vicinity of the pedicle wall 122. As electrostatic pedicle awl 100 moves into pedicle 120, EMG 150 is monitored for nerve excitations. If the tip of electrostatic pedicle awl 100 or its associated electric field 125 breaches the pedicle wall 122, nerve channels are excited and the EMG reacts, generating signals that alert the surgeon to the breach. In practice, the surgeon then withdraws electrostatic pedicle awl 100 and either repositions it or abandons the site altogether.

U.S. Pat. No. 6,796,985 to Bolger, et al. essentially describes an electrostatic pedicle awl with special emphasis on the detection of signals from muscles during the drilling process and operational aspects of generating alerts.

One shortcoming of the prior art electrostatic pedicle awl is that the electric field generated is not well contained. The lack of containment of the electric field often results in false readings. For example, in cases where the pedicle has been previously breached and the awl has been redirected, EMG signals may persist despite a corrected trajectory. Inaccurate EMG signals often lead to false placement failure and unnecessary alternative fixation procedures. Unnecessary procedures cause higher patient morbidity and potential liability.

These similar problems exist in other prior art surgical procedures in which avoidance of nerves is critical, including the extreme lateral interbody fusion procedure ("XLIF procedure"). The XLIF procedure is a method of achieving a direct lateral approach to the intervertebral disc space through the psoas muscle. To perform the XLIF procedure, it is necessary to insert a retractor through the muscle, while avoiding the nerves, to provide an operative corridor to the spine and intervertebral disc space. Once access is achieved, pathology may be addressed as well as insertion of interbody implants.

The psoas muscles, crucial for hip flexion, are found in the lumbar region and are anchored on either side of the spine. The muscles extend into the pelvic area and attach to the hip. Critical nerve roots course within the psoas muscle and must be avoided during surgery to avoid damage and resulting pain or paralysis.

SUMMARY OF INVENTION

One preferred embodiment of the invention includes apparatus and method for creating holes in vertebral pedicles in preparation for transpedicular fixation and avoiding nerves during surgical procedures. The apparatus disclosed includes an electromagnetic awl tool capable of producing time varying magnetic fields. Among other components, the electromagnetic awl is comprised of a core, a tapered awl tip attached to the core and a solenoid assembly for producing a magnetic field. An automatically varying electric current source is provided which generates a time varying magnetic field in the coil. A mechanism is also provided for detecting excitation of nerve cells by an electric field induced by the time varying magnetic field.

In one preferred embodiment, the awl tip is fixed with respect to the solenoid. In this embodiment, a gripping handle is provided attached to the solid core. The current in the solenoid generates a magnetic field. The magnitude and time-derivative of the current at the current source are adjustable so that the magnitude and time derivative of magnetic flux generated is correspondingly adjustable. The current source can produce a set of critically damped or over-damped current pulses. A bipolar alternating current may be produced in another embodiment.

An electromyograh (EMG) is utilized for detecting the excitation of nerve cells due to the breaching or near breaching of a pedicle wall in the vertebral pedicle. A number of preferred locations for the EMG electrodes are taught wherein the nerve excitation signals are best detected; the locations being in the lower extremity of the body and particularly in the vastus lateralis muscle, the medial gastrocnemius muscle and the tibialis anterior muscle.

In an alternate embodiment, an electromagnetic awl is comprised of a core bushing, a tapered metal drill tip inserted into the solid core bushing, a solenoid assembly for producing a magnetic field further comprised of a wire looped around the core bushing, an electric current source attached to the wire so that a time varying magnetic field is generated in the vicinity of the metal drill tip, and a mechanism for detecting the excitation of nerve cells by the time varying magnetic field.

In an alternate embodiment, the drill tip is made to rotate with respect to the solenoid; the rotation being accomplished manually by gripping a handle mechanically attached to the drill tip or by a motor or robot end effector attached to the drill tip.

In an alternate embodiment, the electromagnetic awl is comprised of multiple ceramic core solenoids aligned with parallel axes and who share a common metal drill tip. Each of the separate solenoids produces a magnetic field independently or in conjunction with the other solenoids producing combined electromagnetic effects. Addressing the solenoids in a time varying manner produces a magnetic field with a directional capability with respect to the tapered metal drill tip.

In another alternate embodiment, multiple ferrous rods having solenoids in the handle are mounted with parallel axes and share a single drill tip. By indexing solenoids in the handle, directional magnetic fields can be produced at the drill tip.

In yet another embodiment, the electromagnetic awl is comprised of a single internal solenoid. In this embodiment, the winding of the solenoid is accomplished in a manner which directionally biases the magnetic field that emanates from the drill tip.

In another alternate embodiment, the electromagnetic awl is provided with a ferrous rod with a solenoid assembly in the handle for producing a magnetic field at the tip of the rod.

Yet another embodiment includes a probe or stylus for passing through soft tissues without an associated drill tip.

In yet another embodiment, the probe includes a series of removable tips and cores to accommodate use of differing tools and cannulated implements.

The current generated in the solenoid from the current source in the alternate embodiment generates a magnetic field, the magnitude and time-derivative of the current at the current source is manually adjustable so that the magnitude and time derivative of magnetic flux generated is correspondingly adjustable. The current source produces a set of critically damped or over-damped current pulses or in an alternate embodiment, a bipolar alternating current In one embodiment, an electromyograph (EMG) is utilized for detecting the excitation of nerve cells due to the breaching or near breaching of a pedicle wall in the vertebral pedicle. A number of preferred locations for the EMG electrodes are taught wherein the nerve excitation signals are best detected; the locations being in the lower extremity of the body and particularly on the vastus lateralis muscle, the medial gastrocnemius muscle and the tibialis anterior muscle.

One preferred method disclosed includes use of an electromagnetic awl to create a hole in a vertebral pedicle of a vertebra comprised of the steps of connecting an electromyograph (EMG) to the human body with electrodes placed in the muscles of the lower extremities, placing an electromagnetic awl against a vertebral pedicle, activating the electromagnetic awl to produce an electromagnetic field, rotating the drill tip of the electromagnetic awl to cut and remove material from the given vertebral pedicle, monitoring the EMG for nerve excitation, moving the drill tip within the vertebral body, ceasing movement if an EMG excitation in the muscles of the lower extremities is observed, and removing the electromagnetic awl tool from the vertebral pedicle.

Another preferred method disclosed includes forming a hole is a psoas muscle utilizing an electromagnetic awl including the steps of connecting an EMG to muscles of the lower extremity, monitoring the EMG for nerve excitation, bringing the electromagnetic awl in contact with the psoas muscle, activating the electromagnetic awl to produce an electromagnetic field, advancing the awl in a drilling process to create a passage through a psoas muscle, aborting the drilling process if an EMG excitation is observed, redirecting the awl tool to continue drilling, and removing the awl tool from the psoas muscle.

In the preferred method the drill tip is rotated manually. In an alternative preferred method the drill tip is rotated automatically by a motor of electric or pneumatic means.

Another preferred embodiment includes providing an electromagnetic awl with multiple cores and/or specially wound coils and/or Faraday shields to directionally orient the electromagnetic field with respect to the axis of the electromagnetic awl. In a still further embodiment, an electronic controller sweeps the intensity and position of the electromagnetic field with respect to the axis of the electromagnetic awl while simultaneously displaying the position of the sweep in order to aid in location of the pedicle wall and/or other sensitive nerve tissues.

BRIEF DESCRIPTION OF DRAWINGS

The disclosed inventions will be described with reference to the accompanying drawings, which show important sample embodiments and which are incorporated in the specification hereof by reference, wherein:

FIG. 4a is schematic drawing of a prior art device, namely a pulsed electrostatic pedicle awl in contact with a vertebral pedicle;

FIG. 4b is a schematic drawing of an electromyographic (EMG) instrument used in conjunction with a pulsed current pedicle awl;

FIG. 19 is a cross-sectional drawing of an electromagnetic pedicle awl including a removable core.

FIG. 20 is a cross-sectional drawing of an electromagnetic pedicle awl including a removable handle and tip.

DETAILED DESCRIPTION OF PREFERRED EMBODIMENTS

The numerous innovative teachings of the present invention will be described with particular reference to the presently preferred embodiments (by way of example, and not by way of limitation).

Figures 1, 2:
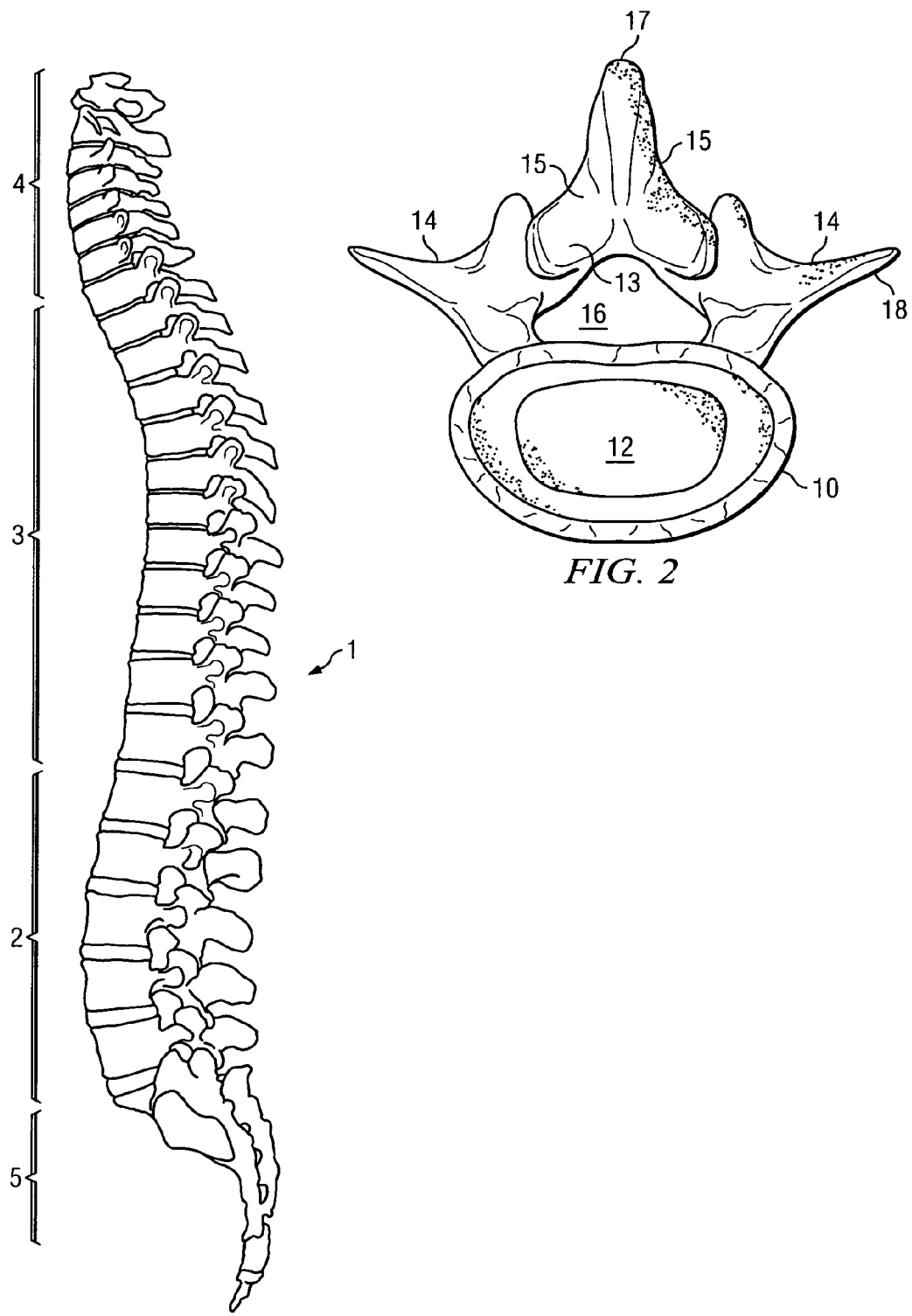
FIG. 1 is a pictorial drawing of the human spine showing the various types of vertebrae.
FIG. 2 is transverse drawing of a lumbar vertebra indicating the morphology of vertebrae significant to the present invention.
Figure 3A:
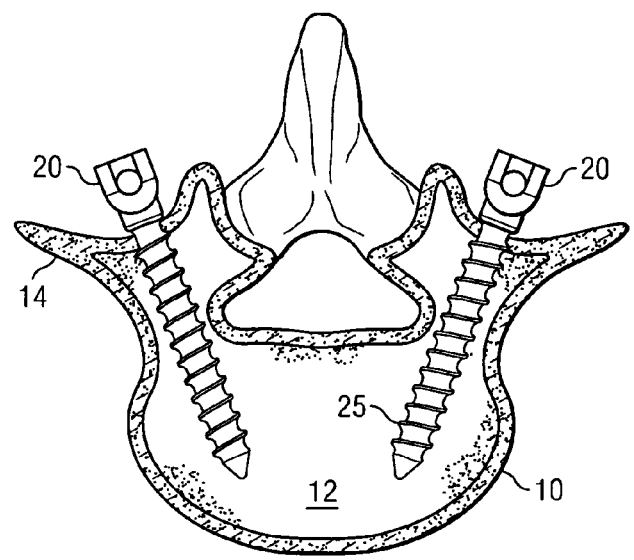
FIG. 3a is a transverse drawing of a general vertebra indicating the placement of pedicle screws in relation to the present invention.
Figure 3B:
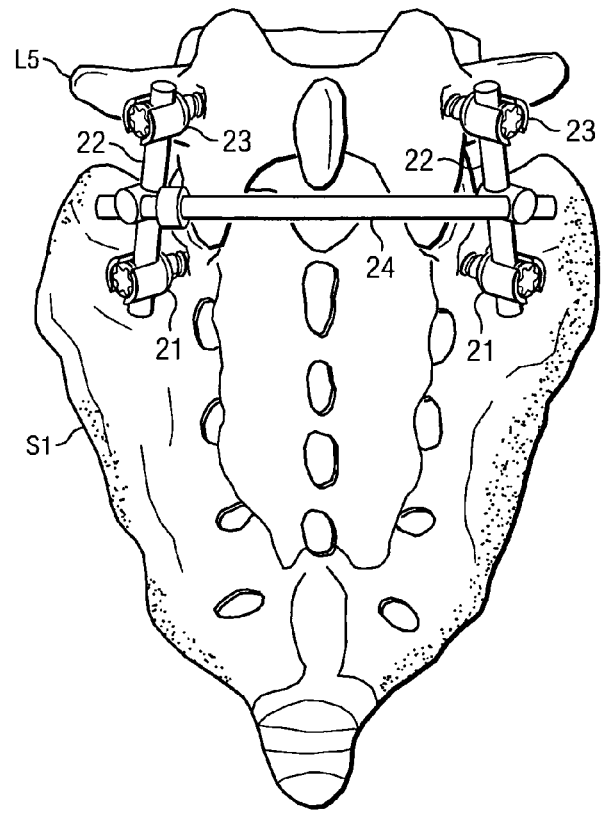
FIG. 3b is an isometric view of lumbar vertebra L5 attached to sacral vertebra S1 via a transpedicular fixation device in relation to the present invention.
Figure 5:
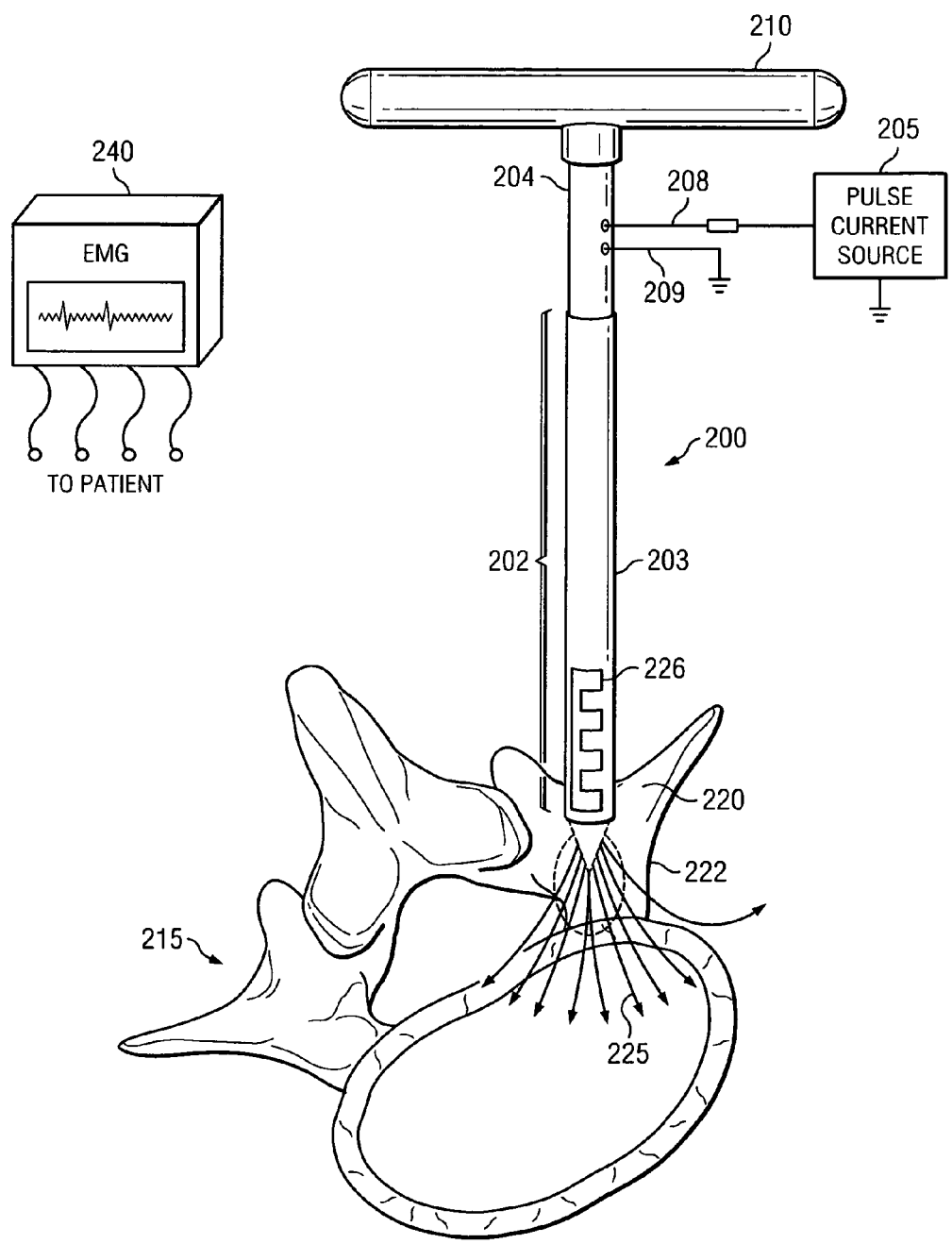
FIG. 5 is a schematic drawing of an electromagnetic pedicle awl in contact with a vertebral pedicle in the preferred embodiment of the present invention.

An electromagnetic pedicle awl is disclosed that utilizes a tightly focused time-varying magnetic flux to create a localized electromotive force (EMF) near the tip of electromagnetic pedicle awl 200 as shown in FIG. 5 and following. The localized EMF creates corresponding localized eddy currents which excite nearby nerves. The excitation is detected by an electromyographic recording device. In comparison to electrostatic pedicle awl 100 of the prior art, electromagnetic pedicle awl 200 excites nerves in close proximity to the tip as opposed to the more general excitation provided by the prior art. Electromagnetic pedicle awl 200 in combination with EMG detector 240 creates a system that is highly sensitive to the pedicle hole position.

According to Faraday's law of induction for time-varying magnetic fields, a voltage or EMF $\epsilon$ is induced by a time-varying magnetic flux (pulsed), $\vec{B}(t)$, and is given by $$\varepsilon = \oint \vec{E} \cdot \vec{dl} = -\frac{d}{dt} \int_S \vec{B}(t) \cdot \vec{dA}$$

where $\vec{E}$ is the induced electric field around a loop and the area integral of $\vec{B} \cdot \vec{dA}$ is taken over the surface area S of the given loop. The effect of the induced EMF $\epsilon$ in the presence of movable charges or ions is to create eddy currents circulating in a loop perpendicular to the direction of magnetic flux $\vec{B}(t)$. In one case, the magnetic flux, $\vec{B}(t)$, pulses on and off with pulse duration $t_d$ and rise time $t_p$.

The classical model of nerve stimulation suggests that $E_{th}$, which is the threshold electric field necessary for a single pulse to excite a nerve to firing, can be expressed as a function of the duration of the pulse d such that:

$$E_{th} = b^*(1 + g/t_d),$$

where b is the rheobase, the empirically-measured minimum field capable of ever exciting the nerve to fire (e.g., for very long pulse durations);

g is the chronaxie, the empirically-measured pulse duration that will permit nerve excitation with a field equal to only twice the rheobase, b, and $t_d$ is the duration of the pulse.

In a simplified illustrative case, a nerve cell may be modeled as tangent to a flat disk at right angles to the magnetic field. A simple approximation for the tangential electric field $E_\phi$, tangent to a loop of radius R, wherein the surface area S enclosed by the loop is considered flat and orthogonal to the magnetic flux $\vec{B}$ is given by application of Faraday's law:

$$E_\phi = -\frac{R}{2}\frac{dB_\perp(t)}{dt}.$$

Therefore, nerve stimulation is elicited if:

$|E_\phi| - E_{th} > 0$ and, $\left|\frac{dB_\perp}{dt}\right| > \frac{2b}{R}\left(1 + \frac{g}{t_d}\right),$ for $t$: $0 < t < t_d$.

Typical values for the human peripheral nerve are:
Rheobase, b: 6-20 V/m for peripheral nerve; and
Chronaxie, g: 200-350 microseconds for peripheral nerve.
Therefore, in the context of the present invention, a pulse duration of 30 µs should require an electric field of order 100 V/m to excite peripheral nerves.

A time varying magnetic flux may be generated by a solenoid coil and may be calculated off-axis as in the paper, "Some Useful Information for the Design of Air-core Solenoids" by D. Bruce Montgomery and J. Terrel, November 1961, Air Force contract AF19(604)-7344, incorporated herein by reference. It is sufficient for the purposes of this disclosure to adopt a numerical simulation of the magnetic field as accomplished by a computer program in order to demonstrate that the potential for eddy current formation and thus nerve excitation falls off rapidly with distance from the electromagnetic awl tip.

In order to produce an electromagnetic field around the electromagnetic awl, pulsed current source 205 produces a time-varying overdamped or critically damped set of current pulses, or alternatively a bipolar alternating current. A suitable pulsed current source for the embodiments of the present invention can be functionally modeled as a series RCL circuit in which a capacitance, C, is charged to an initial voltage, $V_0$, and the charge dumped through a coil, L, and resistance, R.

Figure 9A:
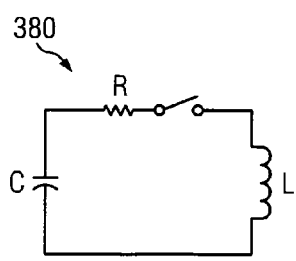
FIG. 9a is a schematic diagram of an RLC circuit suitable for current pulse generation in the preferred embodiment.

FIG. 9a shows circuit 380 for a series RCL circuit model of a pulsed current source for a magnetic stimulator. This circuit is improved by lumping the parasitic capacitance, inductance and impedance of the circuit elements into the values of C, L and R, $R = R_r + R_l + R_c$ $L = L_l + L_c$ $C = C_c + C_l$.

where $R_r$ is the parasitic resistance of the switch, $R_l$ and $L_l$ are the equivalent resistance and inductance of a series R-L model of a coil having a distributed capacity, $C_l$.

The current flow for an initial-value RCL problem is arrived at using elementary circuit analysis (see for example, Smith, R. J., Circuits, Devices and Systems, 4th ed. New York, John Wiley and Sons, 1984). The general solution is $i(t) = A \cdot \exp(-\alpha \cdot t) \cdot \sin(\omega \cdot t)$ where,
i(t) is the current flowing in the circuit at time, t,
A is an amplitude coefficient based upon initial conditions,
α is a damping coefficient such that:

$$\alpha = \frac{R}{2L},$$

t is time in seconds,

ω is the angular frequency in radians per second such that:

$$\omega^2 = \frac{1}{LC} - \frac{R^2}{4L^2}$$

With initial conditions $i(0)=0$, $i(\infty)=0$, and $L(di/dt)=V_0$ at $t=0$, $i(t)$ becomes $$i(t) = \frac{V_0}{\omega L} \cdot \exp(-\alpha \cdot t) \cdot \sin(\omega \cdot t)$$

The magnitude of the magnetic field produced by the coil is proportional to the coil current and the induced electric field is proportional to the time derivative of the current:

$$\frac{di}{dt} = \frac{V_0}{L} \cdot \exp(-\alpha \cdot t) \cdot \left[\cos(\omega \cdot t) - \frac{\alpha}{\omega} \cdot \sin(\omega \cdot t)\right]$$

According to this result, the maximum di/dt, and hence the maximum electric field magnitude, occurs at t=0. The maximum current occurs at the earliest maxima of the current waveform of i(t). Solving the latency to peak current flow, $t_p$, yields:

$$t_p = \frac{1}{\omega} \cdot \tan^{-1}\left(\frac{\omega}{\alpha}\right)$$

After the current reaches a peak at time $t_p$, it falls until the current direction reverses. Note that zeroes of the current function occur when:

$$t = \frac{n\pi}{\omega} : n = 0, 1, 2, \ldots$$

The initial zero occurs when the switch is first closed at t=0. Successive zero-crosses occur when n=1, 2, . . . .

By Kirchoff's Law, the voltage across the capacitor must equal the sum of the voltages across the resistor R and inductor L in FIG. 9a as follows:

$$V_c(t) = i(t)R + L\frac{di}{dt}.$$

If the voltage fraction remaining across the capacitor at any given time is defined as $V_f(t) = V_c(t)/V_0$, then, from substitution of i(t) and di/dt, the voltage fraction can be determined from the equation:

$$V_f(t) = \exp(-\alpha \cdot t) \cdot \left[\cos(\omega \cdot t) + \left(\frac{R}{L} - \alpha\right) \cdot \frac{1}{\omega} \cdot \sin(\omega \cdot t)\right]$$

Figure 9B:
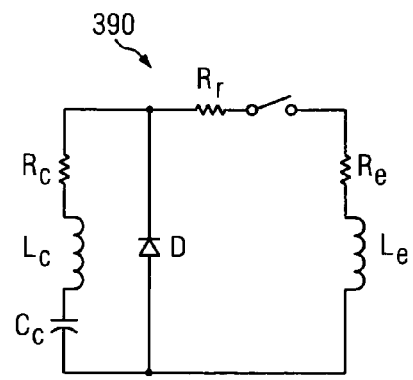
FIG. 9b is a schematic diagram of an RLC circuit with a shunt diode across its capacitor suitable for current pulse generation in the preferred embodiment.

The voltage fraction can be negative which represents a reverse voltage across the capacitor bank. This voltage can be minimized by using a reverse-biased diode shunt D across the capacitor as shown in circuit 390 of FIG. 9b. Since the diode D is in parallel with the capacitor it begins conducting when $V_c$ is negative. Neglecting the diode forward voltage drop, the equation for $V_f(t)$ can be used to determine when the diode conducts by finding the voltage zero preceding a period of negative $V_f$. The latency to diode forward conduction is approximately:

$$t_d = \frac{1}{\omega} \cdot \tan^{-1}\left[\frac{\omega}{\alpha - (R_r + R_l)/L}\right]$$

Notice that the resistance term excludes capacitor internal impedance since it is shunted by the diode.

With the diode forward biased, the coil current is dissipated by the $R_r$ and $R_l$ such that:

$$i_l(t) = i(t_d) \cdot \exp\left(-\frac{(R_r + R_l)}{L} \cdot t\right) \text{ for } t > t_d$$

An advantage of using a diode-capacitor shunt is that the induced electric field is predominately unidirectional. The current pulse has a fast positive rise and a slow decay which results in a magnetic field having a strong initial component in one direction followed by a weak field in the opposite direction.

In the preferred embodiments of the present invention, the pulse generator has approximate component values of inductance L=8.75 μH, capacitance C=7400 μF, resistance R=0.05Ω, a time to peak current, tp of about 400 μs and pulse duration of about 350 μs Charge voltage $V_0$ is about 2 mV and peak current is approximately 0.164 A. A maximum electric field Ep of about 206 V/m is generated in an eddy current loop of dimension 4 to 5 mm. Note that Ep>Eth=100 V/m as calculated previously for nerve stimulation to occur Referring then to FIGS. 5 and 6, an electromagnetic pedicle awl 200 is comprised of central core 204, removable handle 210, solenoid coil 202 encasing central core 204 and pulsed current source 205 for delivering current pulses to solenoid coil 202 via wire 208. Central core 204 has dimensions of approximately 10 cm long and approximately 4 mm in diameter. Threaded hole 211 is provided for removable handle 210. Removable handle 210 is provided with a quick disconnect coupler which may have the feature of a hexagonal socket for coupling with a hexagonal driver attached to central core 204. In one embodiment, removable handle 210 is provided with a solid rod extension between the grip and the coupler to extend the reach of the device.

Central core 204 includes drill tip 207 suitable for making pilot holes in bonelike material. In another embodiment the core may be hollow with a removable stylus. The removable stylus aids in cleaning and is used to fit the device with differing stylus tops for various procedures. Solenoid coil 202 includes a wire coil around the non-conductive central core 204. Solenoid coil 202 is singly wound approximately one hundred twenty five (125) turns of 22 AWG insulated copper wire with one end of the wire brought through center hole 206 of central core 204 and out near the handle as wire 208. Wire 208 is connected to pulsed current source 205. Wire 209 is locally grounded. In an alternate embodiment, wires 208 and 209 are connected to pulsed current source 205 with differential electrical outputs. The wires are connected through a rotary coupling 295 which mechanically provides for the rotation of the handle and the core with respect to the wires.

In one preferred embodiment, central core 204 is constructed of a material with low magnetic permeability such as a hardened ceramic. A particulate reinforced oxide and non-oxide composite is preferred to increase mechanical toughness while maintaining low magnetic permeability. Drill tip 207 includes a diamond point or a chisel type configuration for cutting bone material. Drill tip 207 includes a base substrate of low magnetic permeability material such as a hardened ceramic In another preferred embodiment central core 204 contains a material with low coercitivity and high magnetic permeability such as silicon steel or permalloy. Drill tip 207 includes a base substrate of high magnetic permeability material such as a hardened steel. In this case, a radial slot is provided along the longitudinal axis of the central core. The radial slot eliminates or greatly reduces eddy currents that may be generated in the high magnetic permeability central core. The eddy currents are disfavored because they consume energy from the magnetic field being generated by the solenoid and hence reduce its efficiency.

Solenoid coil 202 is covered with a non-conductive polymer sheathing 203 so that the surface of pedicle awl 200 is smooth and so that the direct coil drive currents are electrically isolated from the patient. In yet another embodiment a comb-shaped Faraday shield 226 may be incorporated circumferentially between solenoid coil 202 and outer polymer sheathing 203 to prevent capacitively coupled electrical stimulation of the nearby nerve tissue. The Faraday shield may also be shaped and positioned to direct the intensity of the electromagnetic field as will be more fully described later. Drill tip 207 outer radius is made to be slightly larger than the outer surface radius so that pedicle awl 200 may easily penetrate into the vertebra without obstruction.

The region of nerve excitation 130 is determined by the rapidity of change of magnetic flux 225 near the tip. Typically, the pulsed current source 205 is made to be adjustable in magnitude and in its pulse characteristics such as rise and fall times. Time varying magnetic flux 225 in turn induces a localized EMF and corresponding eddy currents in the vicinity of drill tip 207.

Figure 10A:
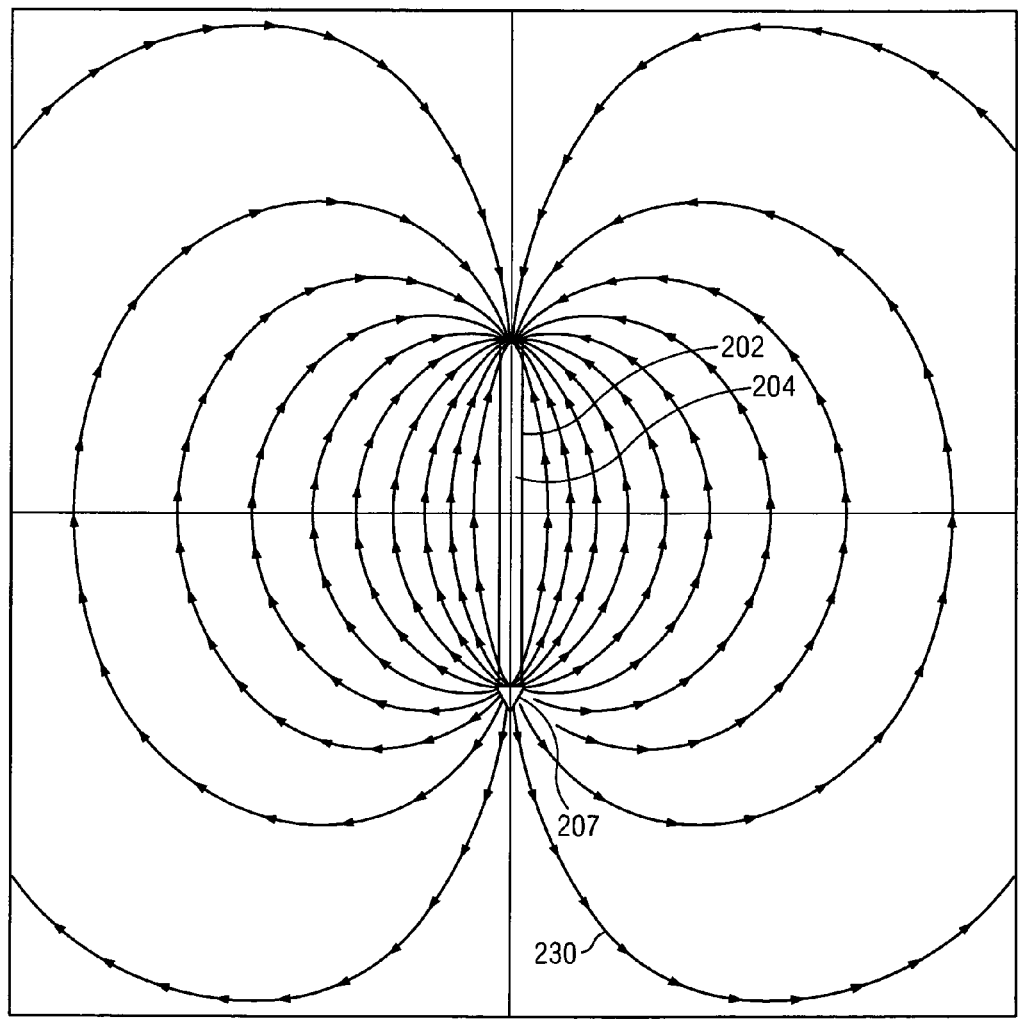
FIG. 10a is a magnetic field vector diagram showing the magnetic field lines of an electromagnetic pedicle awl in the preferred embodiment of the present invention constructed with a core and drill tip of magnetic permeability 1.0.

FIG. 10a shows an example of plot 500 magnetic field lines 230 generated from pedicle awl 200 where central core 204 and drill tip 207 has a magnetic permeability of 1.1 corresponding to a hardened ceramic material; solenoid coil 202 generates the magnetic field for the same pedicle awl parameters.

Figure 10B:
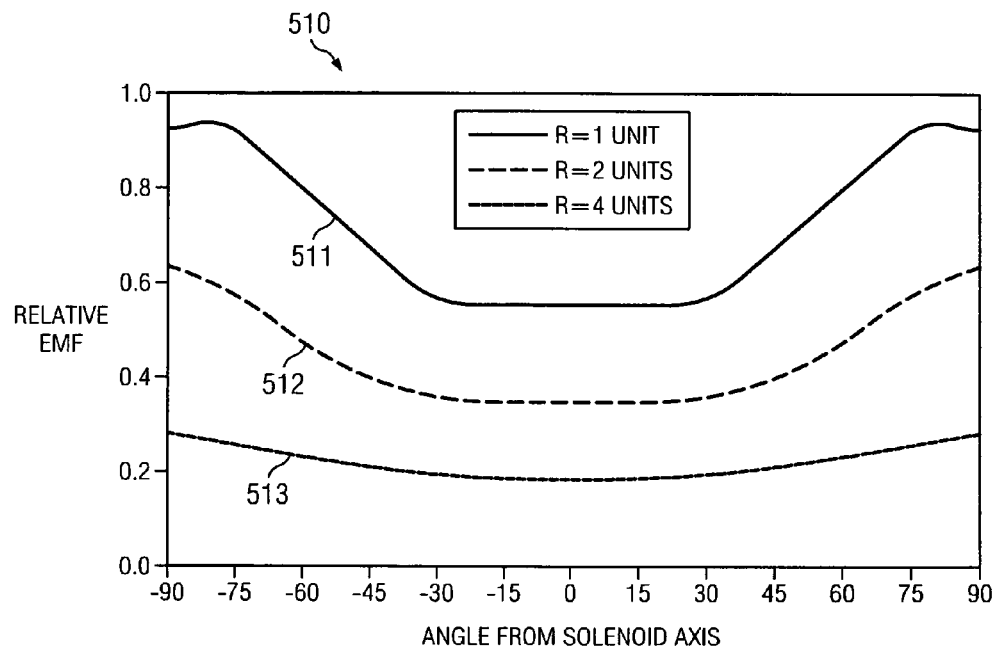
FIG. 10b is a set of plots of the relative magnetic flux for a given current time-rate of change in the preferred embodiment of the present invention where the core and drill tip is made of material with magnetic permeability 1.0.

EMF produced in loops surrounding drill tip 207 will follow the characteristics of magnetic flux strength generated at surrounding points, since only a time rate of change of current, di/dt, in solenoid coil 202 is causing the magnetic flux to change. Relative magnetic flux from one point to another will indicate the relative EMF produced for a given current rate of change. Relative EMF means EMF at a given spatial point normalized to the EMF that produced at the center of the tip. FIG. 10b includes plot 510 of the relative magnetic flux produced at points in a spherical arc of radius, r, centered on the tip of the drill tip and at three fixed distances r from the center of drill tip 207 wherein the relative magnetic flux is the ratio of the magnetic flux at points r to the magnetic flux at the tip, $|Br|/|B0|$.

The distances, r, are measured in units of solenoid diameter: r=1 unit means that the curve 511 was generated for points at a distance of one solenoid diameter from the tip, curve 512 for points at a distance of two solenoid diameters from drill tip 207 and curve 513 for points at a distance of four solenoid diameters from drill tip 207. The points on the arc are plotted according to their angle where zero degrees is along the axis of pedicle awl 200, +90 degrees is perpendicular to the axis of pedicle awl 200 and to the right of drill tip 207 and −90 degrees is perpendicular to the axis of pedicle awl 200 and straight to the left of drill tip 207.

Plot 510 shows that where central core 204 is made of a hardened ceramic, the magnetic field flux is relatively confined, having degraded by 80% at a distance of 4 (four) solenoid diameters from the center drill tip 207. Furthermore, plot 510 indicates that the relative magnetic flux varies by approximately 40% from the forward direction to the sides, increasing toward the sides. This instrument is more likely to produce eddy current stimulation of nerves to the side than to the forward direction.

Figure 11B:
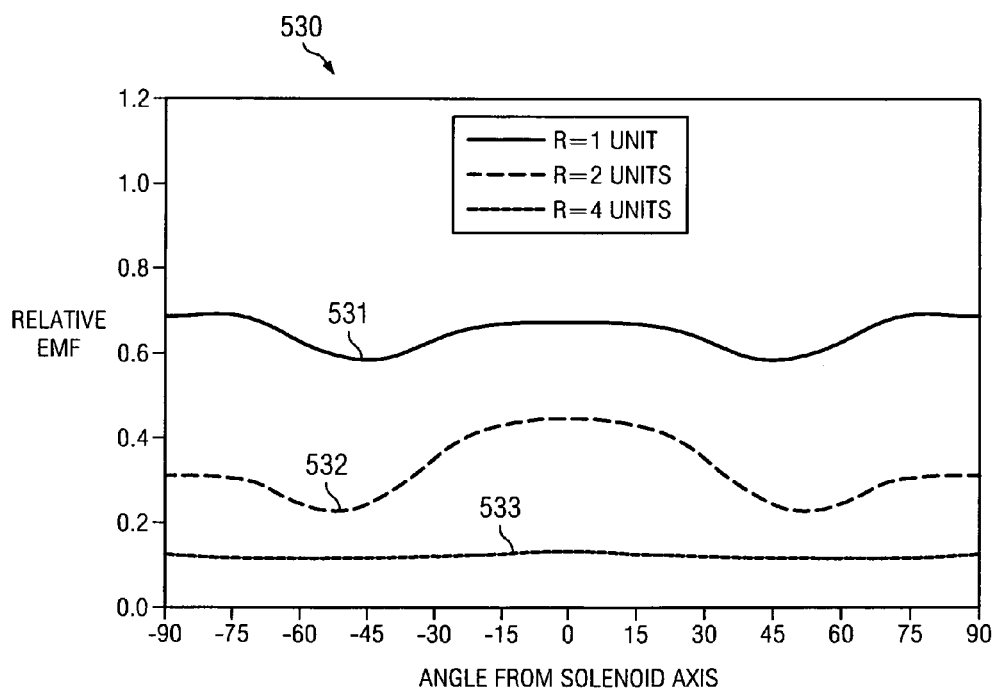
FIG. 11b is a set of plots of the relative magnetic flux for a given current time rate of change in the preferred embodiment of the present invention where the core and drill tip is made of material with magnetic permeabilities 5000 and 300, respectively.
Figure 11A:
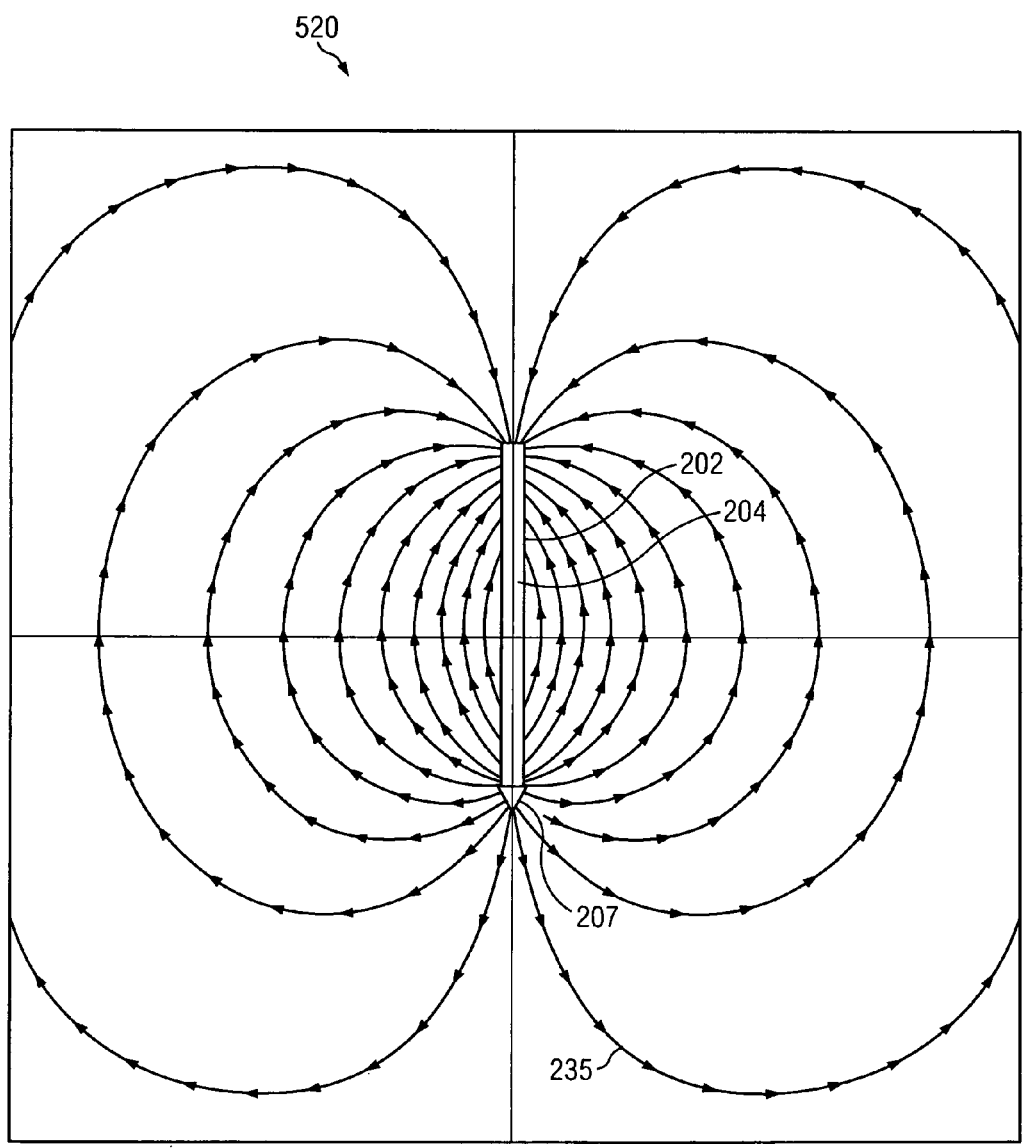
FIG. 11a is a magnetic field vector diagram showing the magnetic field lines of an electromagnetic pedicle awl in the preferred embodiment of the present invention constructed with a core and drill tip of magnetic permeabilities, 5000 and 300, respectively.

As another example, FIG. 11a shows plot 520 of magnetic field lines 235 generated from pedicle awl 200 where the central core 204 and drill tip 207 have a magnetic permeability of 5000 (typical of iron) and drill tip 207 has a magnetic permeability of 300 (typical of stainless steel); solenoid coil 202 generates the magnetic field for the same pedicle awl parameters.

FIG. 11b shows a plot 530 of the relative magnetic flux produced at points in spherical arcs of radii, r, centered on the tip of the drill tip and at three fixed distances from drill tip 207 wherein the relative magnetic flux is the ratio of the magnetic flux at points r to the magnetic flux at the tip, $|Br|/|B0|$. Curve 531 was generated for points at a distance of one solenoid diameter from drill tip 207. Curve 532 was generated for points at a distance of two solenoid diameters from drill tip 207. Curve 533 was generated for points at a distance of four solenoid diameters from drill tip 207. The points on the arc are plotted according to their angle where zero degrees is along the axis of pedicle awl 200, +90 degrees is perpendicular to the axis of pedicle awl 200 and to the right of drill tip 207 and −90 degrees is perpendicular to the axis of pedicle awl 200 and straight to the left of drill tip 207.

Plot 530 shows that where central core 204 has a high magnetic permeability, the magnetic field flux is well confined, having degraded by almost 90% at a distance of four solenoid diameters from the center drill tip 207. Furthermore, plot 530 indicates that the relative magnetic flux does not vary significantly from the forward direction to the sides, except for a 20-30% dip near a 45 degree angle from the axis of solenoid coil 202.

In another embodiment electromagnetic probe for probing soft tissue is conceived wherein a pilot hole is not required and thus a drill tip is not required. FIG. 19 is a cross-sectional drawing of a probe for passing through soft tissue such as a human muscle. Probe 1900 has solid core 1902 machined to sharp point 1903. Probe 1900 has solenoid coil 1904 around solid core 1902 and non-conductive external cover 1906 covering solenoid coil 1904. Solenoid coil 1904 is energized to create a time-varying magnetic field in the vicinity of point 1903.

In yet another embodiment, the electromagnetic awl utilizes an air core instead of a solid core for transmitting magnetic flux through a solenoid coil. FIG. 20 is a cross sectional drawing of electromagnetic awl 1950 comprising a non-conductive cylindrical tube 1952 with threads 1957 tapped at a lower end and threads 1961 tapped at an upper end. Electromagnetic awl 1950 further comprises solenoid coil 1954 around cylindrical tube 1952 and non-conductive external cover 1956 covering solenoid coil 1954. Drill tip 1958 with threads 1959 is fastened into the lower end of electromagnetic awl 1950 such that threads 1959 are mated with threads 1957. Handle 1960 with threads 1962 is fastened onto the upper end of electromagnetic awl 1950 such that threads 1962 are mated with threads 1961. Alternatively, a vertically oriented handle with long axis along the same axis as electromagnetic awl 1950 may be used in place of the horizontally oriented handle as shown. Other ways of fastening the handle and the drill tip to the cylindrical tube may be used; such as a suitable epoxy adhesive.

Figure 12:
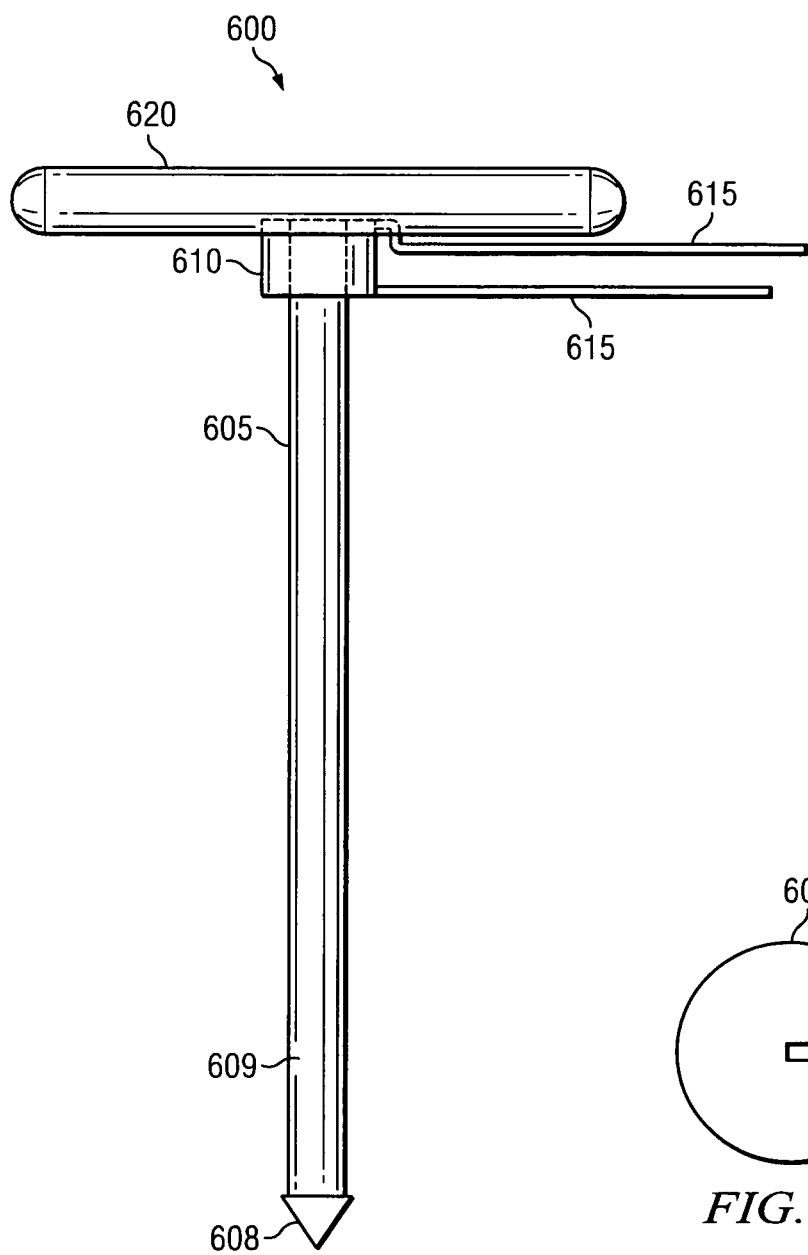
FIG. 12 is a cross-sectional drawing of a side view of the electromagnetic pedicle awl in an alternate embodiment of the present invention where the solenoid coil is integrated into the handle of the electromagnetic pedicle awl and the core rod of the electromagnetic pedicle awl is made of high magnetic permeability material.
Figure 13:
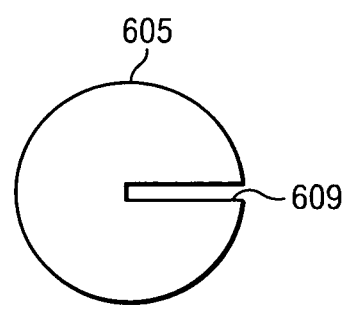
FIG. 13 is a cross-sectional drawing of a top-view of the core rod of the electromagnetic pedicle awl in an alternate embodiment of the present invention.

An alternate embodiment of the present invention is shown in FIG. 12 as electromagnetic pedicle awl 600. Pedicle awl 600 is constructed of core rod 605 to which is attached a handle 620 and drill tip 608. Handle 620 may be connected to core rod 605 by a quick disconnect or by threaded screw or by other suitable means. Drill tip 608 may be machined as part of core rod 605 or it may be a removable tip capable of replacement. Solenoid coil 610 is mechanically integrated into handle 620 using epoxy or other suitable means and surrounds core rod 605 near its handle end. Referring to FIGS. 12 and 13, core rod 605 and drill tip 608 include radial slot 609 along their longitudinal axes in order to reduce eddy currents within core rod 605.

Solenoid coil 610 in this preferred embodiment is a multi-layer coil having approximately 200 wraps. Solenoid coil 610 is connected via wires 615 to a pulsed current source. When pulses of current are sent through solenoid coil 610 a magnetic flux is generated internal to its coil and core rod 605. Core rod 605 is preferably made with a high permeability metal such as iron or steel. The core rod serves as a magnetic conduit for magnetic flux to propagate from solenoid coil 610 down and through drill tip 608. Drill tip 608 is also made of a material with significant magnetic permeability such as steel.

Figure 14A:
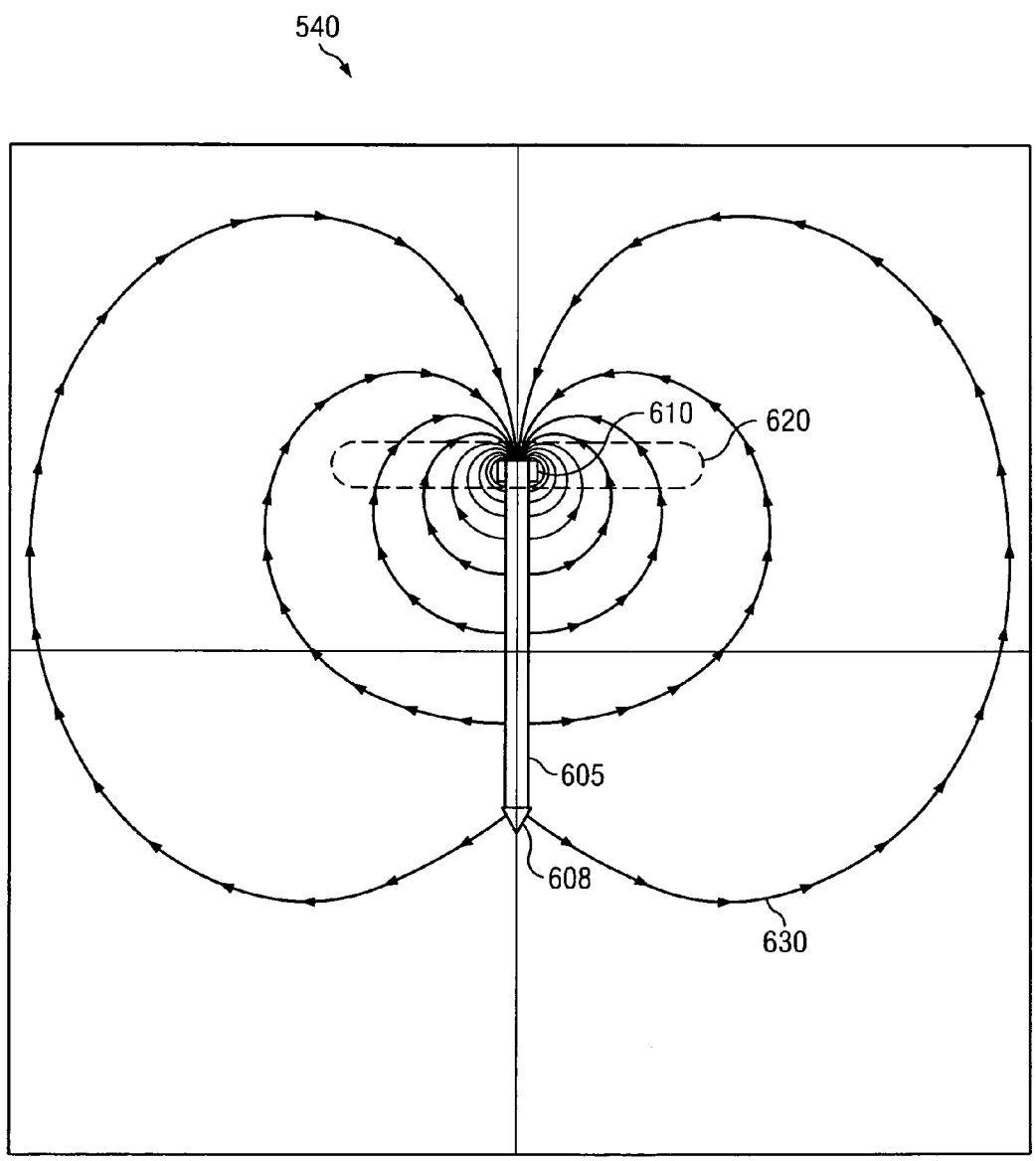
FIG. 14a is a magnetic field vector diagram showing the magnetic field lines of an electromagnetic pedicle awl in an alternate embodiment of the present invention constructed with a core and drill tip of magnetic permeabilities, 5000 and 300, respectively and wherein the solenoid coil is integrated into the handle of the pedicle awl.

FIG. 14a shows a plot 540 of magnetic field lines 630 generated from pedicle awl 600 where the core rod 605 has a magnetic permeability of 5000 and drill tip 608 has a magnetic permeability of 5000; solenoid coil 610 generates the magnetic field.

EMF produced in loops surrounding drill tip 608 will follow the characteristics of magnetic flux strength generated at surrounding points, since only a time rate of change of current, di/dt, in solenoid coil 610 is causing the magnetic flux strength to change. Relative magnetic flux field from one point to another will indicate the relative EMF produced for a given current rate of change.

Figure 14B:
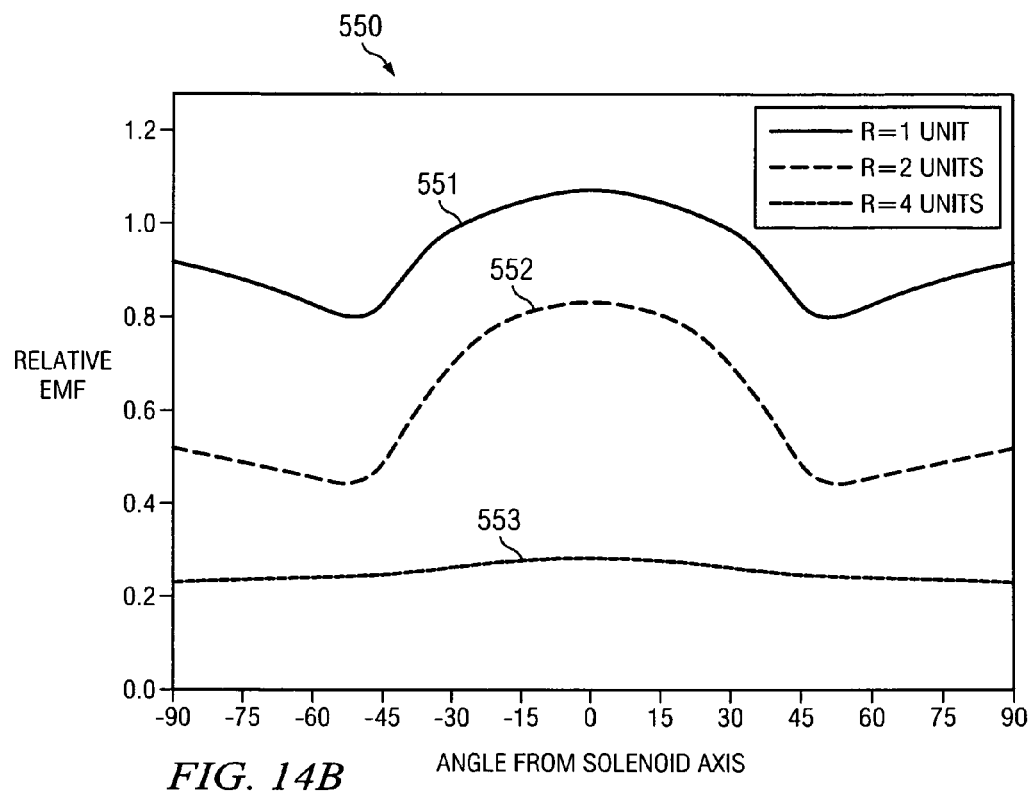
FIG. 14b is a set of plots of the relative magnetic flux for a given current time rate of change in an alternate embodiment of the present invention where the core and drill tip is made of material with magnetic permeabilities 5000 and 300, respectively and where the solenoid coil is integrated into the handle of the electromagnetic pedicle awl.

In FIG. 14b is plot 550 of the relative magnetic flux produced at points in spherical arcs of radii, r, centered on drill tip 608 and at three fixed distances r from drill tip 608 wherein the relative magnetic flux is the ratio of the magnetic flux at points r to the magnetic flux at the tip, $|Br|/|B0|$.

The curve 551 was generated for points at a distance of one solenoid diameter from drill tip 608. Curve 552 was generated for points at a distance of two solenoid diameters from drill tip 608 and curve 553 was generated for points at a distance of four solenoid diameters from drill tip 608. The points on the arc are plotted according to their angle where zero degrees is along the axis of pedicle awl 600, +90 degrees is perpendicular to the axis of pedicle awl 600 and to the right of drill tip 608 and −90 degrees is perpendicular to the axis of pedicle awl 600 and straight to the left of drill tip 608.

Plot 540 of FIGS. 14a and 550 of FIG. 14b show that where core rod 605 is made of a high magnetic permeability material, the magnetic field flux is relatively confined, having degraded by about 75% at a distance of four solenoid diameters from the center drill tip 608. Furthermore, plot 550 indicates that the relative magnetic flux varies by approximately 30% to 40% from the forward direction to the sides, increasing toward the forward direction. This instrument is more likely to produce eddy current stimulation of nerves to the forward direction than to the sides.

Figure 15A:
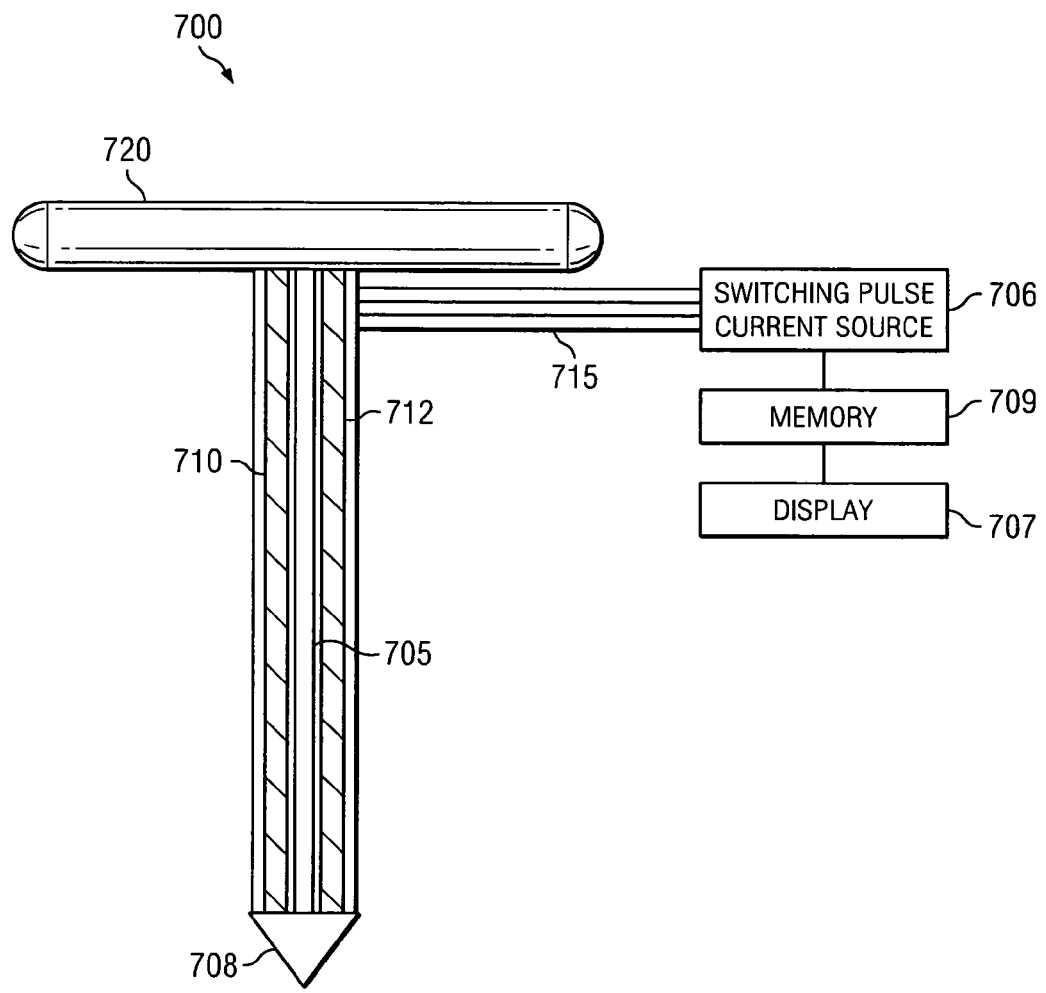
FIG. 15a is a cross-sectional drawing of the side view of an electromagnetic pedicle awl consistent with an alternate embodiment of the present invention where the electromagnetic pedicle awl contains multiple solenoid coils.
Figure 15B:
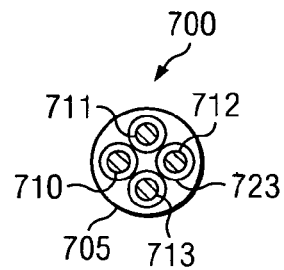
FIG. 15b is a cross-sectional drawing of the top view of an electromagnetic pedicle awl consistent with an alternate embodiment of the present invention where the electromagnetic pedicle awl contains multiple solenoid coils.

Another alternate embodiment of the present invention is shown in the cross-section drawings of FIGS. 15a and 15b as pedicle awl 700. Pedicle awl 700 is comprised of four solenoid coils encased within a core assembly 705 to which is attached a handle 720 and drill tip 708. Wire leads 715 are attached to each solenoid coil sufficient to independently drive a current through each solenoid coil. Typical dimensions for pedicle awl 700 is an outer surface diameter of about 4.5 mm, solenoid coil diameter 723 of 1.6 mm, and length from handle 720 attachment point of core assembly 705 to drill tip 708 attachment point of core assembly 705, approximately 7 cm and the solenoids use 32 AWG magnet wire. In the currently described embodiment, the central cores of each solenoid, the core assembly 705 and drill tip 708 are made of a low magnetic permeability material. Alternate embodiments include high magnetic permeability materials used for the core assembly and drill tip.

Wire leads 715 are attached to a switching pulsed current source 706. The switching pulsed current source 706 is connected to a digital controller 709 and display 707. The digital controller energizes each solenoid coil in a rotating sequence over time thereby producing a rotating directional field. The rotating sequence in the preferred embodiment ranges from about 1 cycle per second to about 25 cycles per second. The given arrangement of solenoid coils for pedicle awl 700 allows for directional probing for nearby nerves. As each coil is energized, the side nearest the energized coil will generate a larger magnetic flux strength which in turn will interact most strongly with nerves in its vicinity. The position of the active coil is shown relative to the handle by a graphic display generated by the controller and displayed on display 707. The rotating directional field is useful in applications where the location of the nerve with respect to the axis of the awl is important. The rotating directional field is also useful in robotic applications as a feed back mechanism for correcting the entry angle of the awl during surgery.

In an alternate embodiment, more than one coil may be energized at a time to produce different geometries of magnetic flux strength. For example, in one embodiment, a four-coil geometry is adopted, having coils 180 degrees apart with respect to the axis of the pedicle awl. Each coil can be energized with current of differing polarization, producing opposite fields in the respective coils. The opposite fields in adjacent coils produce a distinctively biased magnetic field. In use, as two opposing energized coils are de-energized the opposing coils immediately clockwise are energized according to the polarity of its immediate neighbor in a rotating fashion. The process effectively creates rotating magnetic flux "beam" which sweeps about the pedicle awl with respect to its longitudinal axis at rotation speed set by the digital controller.

In yet another embodiment of the present invention, a useful display is created by digitally combining the radial position of the energized coil with digital EMG signals within the digital controller. A graphical correlation of the EMG signal strength with a magnetic field position creates a graphical map of the nerve cells. In the case of vertebral pedicles, the graphical map represents a map of the pedicle wall. In the case of the psoas muscle, the graphical map represents the location of peripheral nerves to be avoided.

Figure 16B:
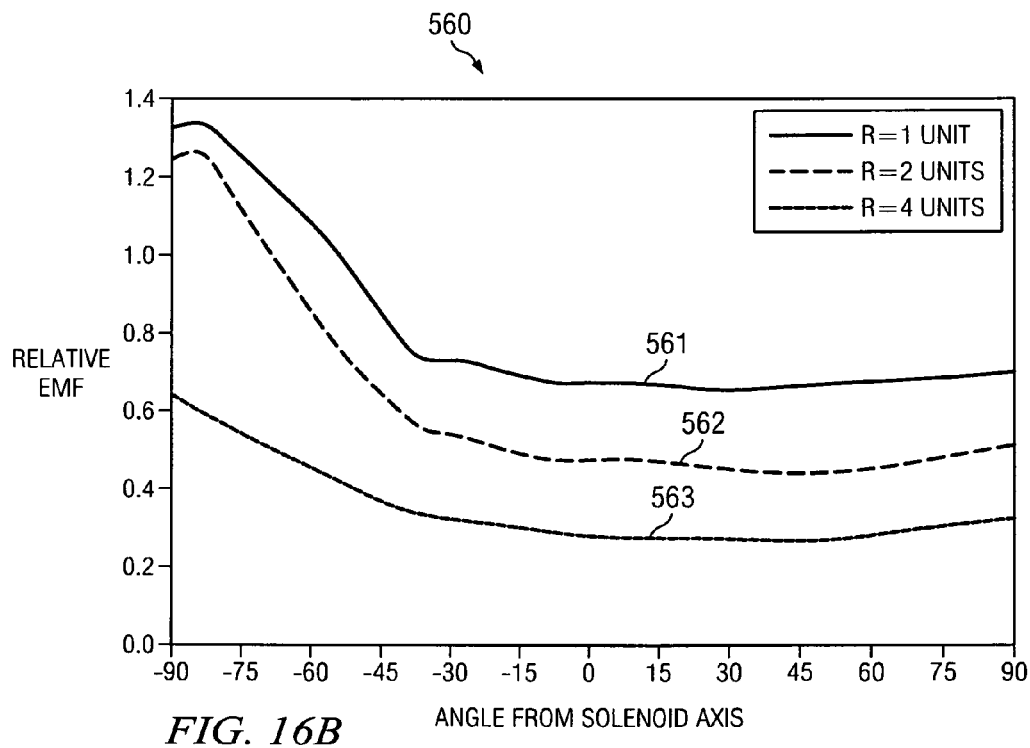
FIG. 16b is a set of plots of the relative magnetic flux for a given current time rate of change in an alternate embodiment of the present invention constructed with multiple solenoid coils.
Figure 16A:
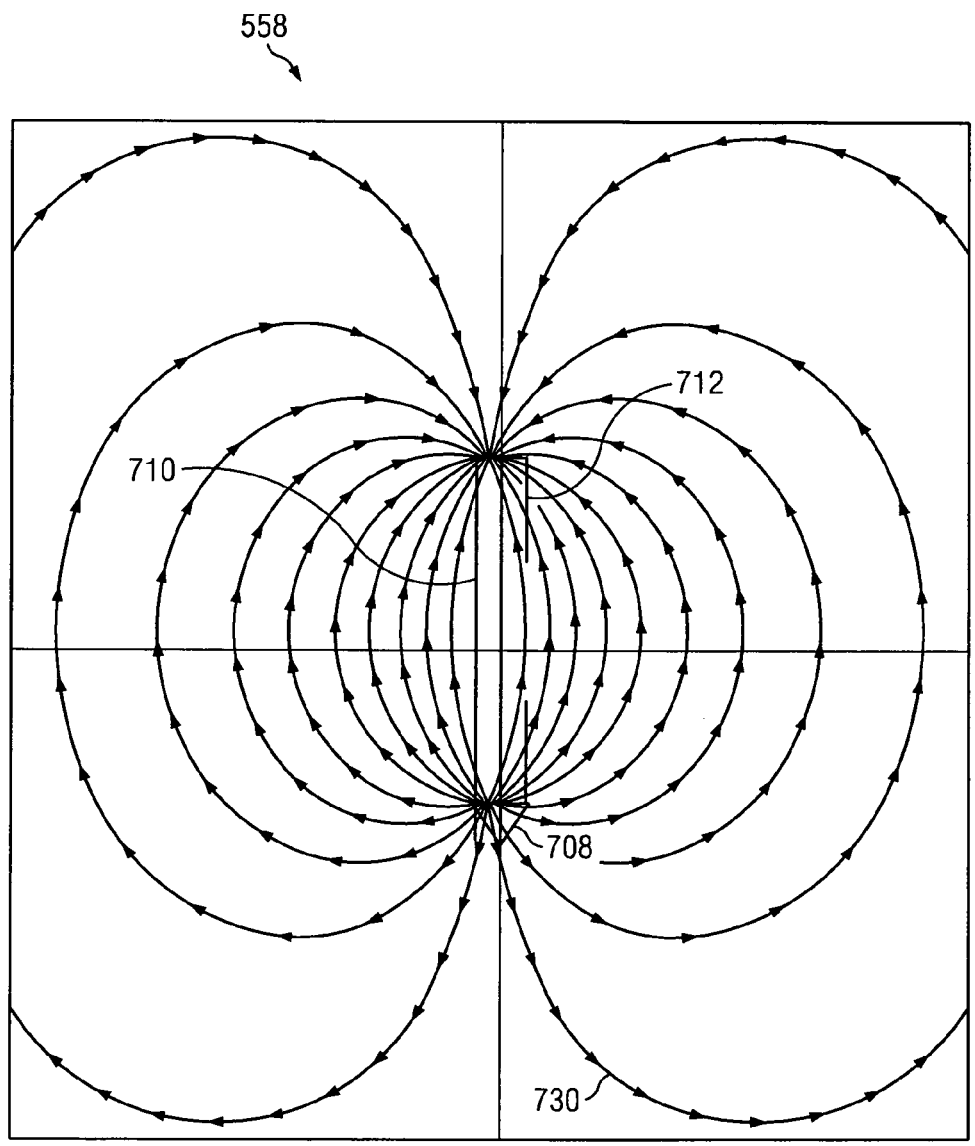
FIG. 16a is a magnetic field vector diagram showing the magnetic field lines of an electromagnetic pedicle awl in an alternate embodiment of the present invention constructed with multiple solenoid coils.

FIG. 16a is plot 558 of magnetic field lines 730 generated from pedicle awl 700 for a given situation where the leftmost solenoid coil 710 is energized. Solenoid coil 710 generates the magnetic field as shown. The magnetic field lines are clearly skewed to the left, offset by the position of solenoid coil 710 with respect to the center axis of core assembly 705. The plots of FIGS. 16a and 16b were generated for the pedicle awl parameters $M_{rod}$=5000, $M_{solenoid\ core}$=5000.

EMF produced in loops surrounding drill tip 708 will follow the characteristics of magnetic flux strength generated at surrounding points, since only a time rate of change of current, di/dt, in solenoid coil 710, solenoid coil 711, solenoid coil 712 or solenoid coil 713 is causing the magnetic flux to change. In FIG. 16b is plot 560 of the relative magnetic flux produced at points on spherical arcs of radii, r, centered on drill tip 708 and at three fixed distances r from drill tip 708 wherein the relative magnetic flux is the ratio of the magnetic flux at points r to the magnetic flux at the tip, |Br|/|B0|.

Curve 561 was generated for points at a distance of one solenoid diameter from tip 708. Curve 562 was generated for points at a distance of two solenoid diameters from drill tip 708. Curve 563 was generated for points at a distance of four solenoid diameters from drill tip 708. Solenoid diameters for solenoid coil 710, solenoid coil 711, solenoid coil 712 and solenoid coil 713 are shown to be identical, but may be different in other embodiments of the present invention.

Plot 560 shows that according to the alternative embodiment of the present invention, wherein core assembly 705 is made of a high magnetic permeability material, the magnetic field flux is relatively confined on one side but not on the other, having degraded by about 75% at a distance of four solenoid diameters from drill tip 708 to the right side. Plot 560 indicates that the relative magnetic flux varies by approximately 50% to 60% from the left side direction to the right side direction, increasing toward the left side direction. This instrument, with solenoid coil 710 energized, is more likely to produce eddy current stimulation of nerves to the left side direction than to the front or to the right side. Not shown are similar curves when the other three solenoids are energized which may be inferred by symmetry.

Figures 7A, 7B, 8:
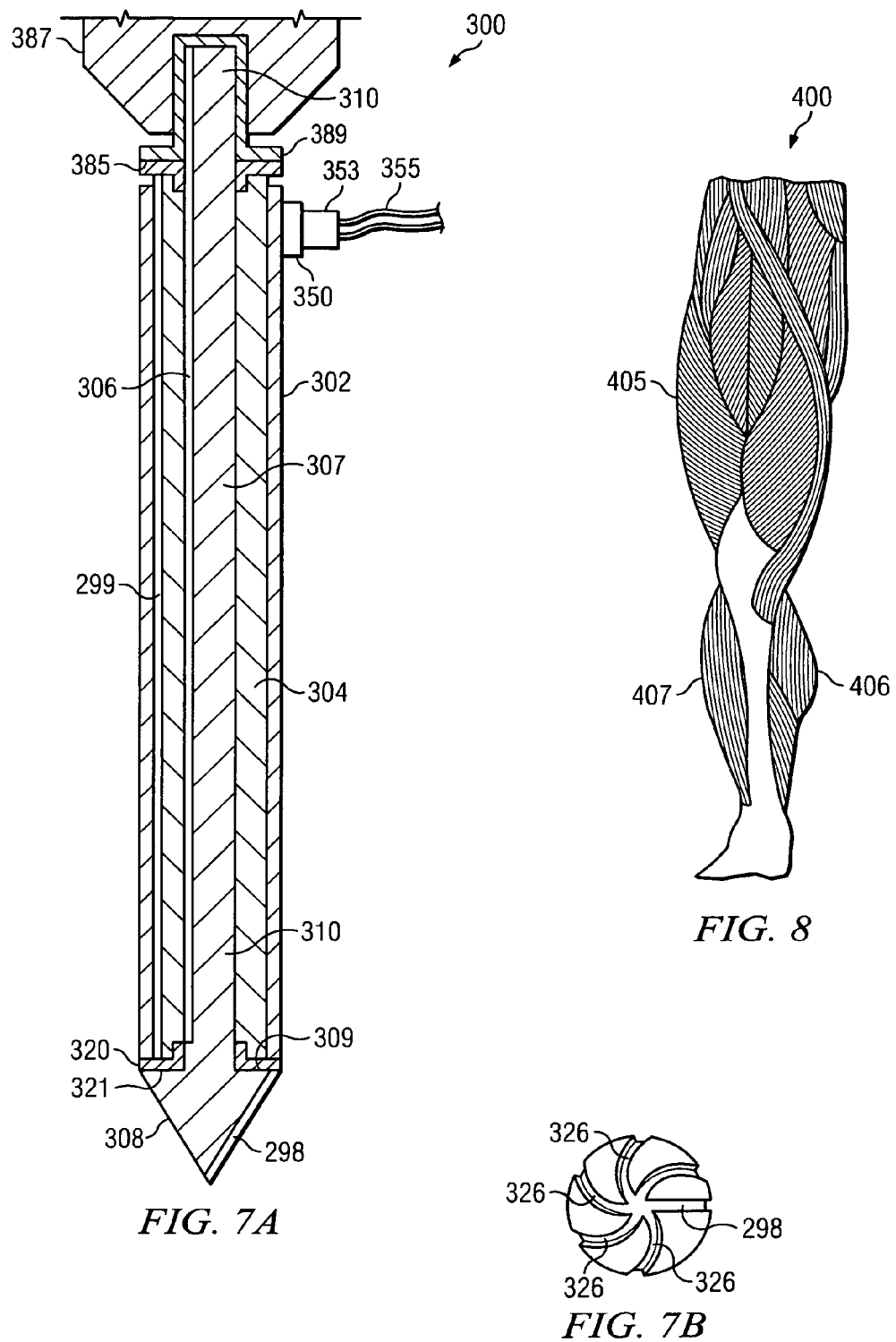
FIG. 7a is a cross-section view of an electromagnetic pedicle awl motivated by a powered chuck in an alternate embodiment of the present invention.
FIG. 7b is an end view of a drill tip of an electromagnetic pedicle awl in an alternate embodiment of the present invention.
FIG. 8 is a pictorial diagram illustrating a preferred electrode arrangement for monitoring a patient's EMG signals while using the electromagnetic pedicle awl in accordance with the present invention.

In FIGS. 7a and 7b, a cross-sectional view of an alternate embodiment of the present invention is shown. Electromagnetic pedicle awl sub-assembly 300 is comprised of awl 307, central core bushing 304 for holding awl 307, including shaft 310, solenoid coil 302 surrounding core bushing 304 and a multi jawed chuck 387 for gripping the awl and rotating it with respect to core bushing 304. Shaft 310 extends out of core bushing 304 and is attached by the chuck. Shaft 310 includes longitudinal slot 306 to reduce eddy current. Solenoid coil 302 is mechanically fixed to core bushing 304. Awl 307 rotates with respect to core bushing 304. A forward thrust bearing 389 is rigidly attached to shaft 310. Forward thrust bearing 389 is directly adjacent to and in sliding contact with forward thrust surface 385 on core bushing 304. A rear thrust bearing 320 is provided on shaft 310 adjacent drill tip 308 and is rigidly attached to shaft 310. Rear thrust bearing 320 is adjacent to and in sliding contact with rear thrust surface 321 on drill tip 308. In use, the forward thrust surface and forward thrust bearing in cooperation provide sufficient force to maintain the axial position of the core bushing with the shaft during forward drilling operations. The reverse thrust bearing and reverse thrust surface in cooperation maintain the axial position of the shaft and the core bushing as the awl is withdrawn from the pedicle.

The two ends of the coil are connected to connector block 350 which is positioned on the exterior of the solenoid coil 302 and is stationary during the rotation of the drill. The connector block serves as an electrical connection point for connector 353 which is connected to wires 355 that provide drive current for the solenoid coil. Drill tip 308 includes the features of a conical surface with shoulder 309 sufficient to move material away from the outer surface of solenoid coil 302. The chuck in turn is attached to a handle such as that described in relation to FIG. 6 or attached to a robot end effector. In yet another embodiment, a motor or impact wrench may be attached to the chuck so that controlled rotation and axial impacts may be delivered to the awl. Solenoid coil 302 is connected to a time-varying current source which may produce overdamped, critically damped current pulses or a bipolar alternating current.

Awl 307 is preferably made of a non-conductive material and may be a machined composite ceramic. Core bushing 304, preferably made with a non-ferromagnetic material, has a slot 299 along its axis to avoid the buildup of eddy currents. Alternatively core bushing 304 may be made of a machined ceramic. Referring to FIGS. 7a and 7b, drill tip 308 is similar to a twist drill bit and is preferably made with a non-ferromagnetic material with straight slot 298 along its axis to avoid eddy currents. FIG. 7b shows an end view of drill head 308. In this view, an alternate configuration is shown having a series of helical slots 326 that function to eliminate eddy currents in drill tip 308 and move debris out of the way during use.

Figure 17A:
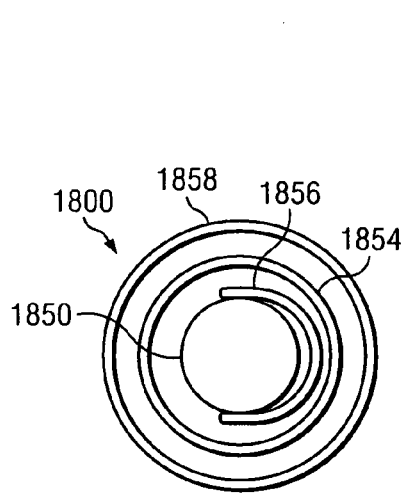
FIG. 17a is a cross-sectional drawing of an electromagnetic pedicle awl consisting of an alternate embodiment of the present invention where the electromagnetic pedicle awl contains a solenoid coil arranged to direct a magnetic field.
Figure 17B:
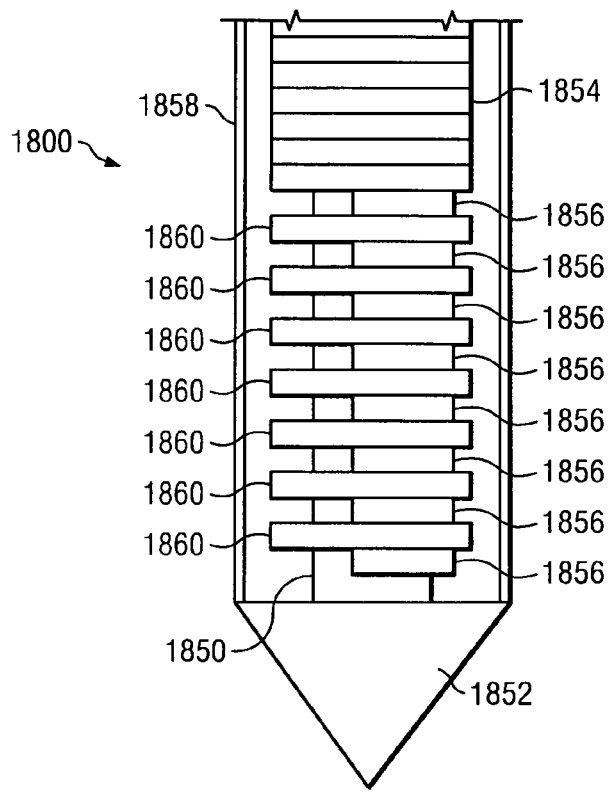
FIG. 17b is a cross-sectional drawing of a side view of an electromagnetic pedicle awl consistent with an alternative embodiment of the present invention comprising a solenoid coil arranged to direct a magnetic field.

FIGS. 17a and 17b show yet another embodiment of the present invention. In this embodiment, an awl 1800 is provided with a central nonconductive core 1850. Around the central nonconductive core, a coil 1854 is placed including return windings 1856 and complete windings 1860. Return windings 1856 double back around 180° of the circumference of the non-conductive core for every complete rotation of the complete windings 1860. The return windings operate to cancel the magnetic field generated by the complete windings 1860 immediately adjacent.

The awl is covered with a non-conductive external cover 1858 and fitted with drill tip 1852.

Figure 18:
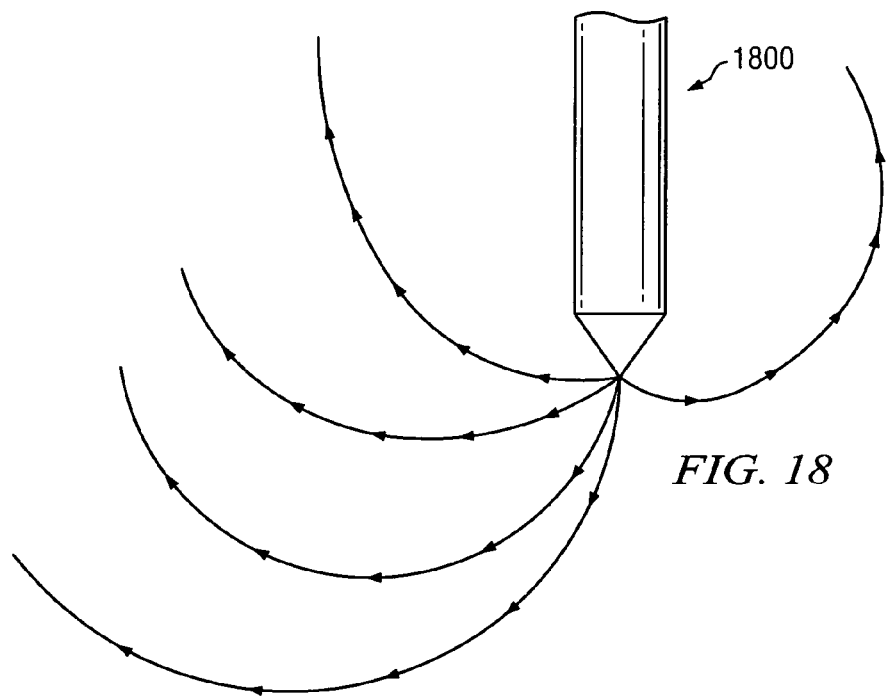
FIG. 18 is a magnetic field vector diagram showing the magnetic field lines of an electromagnetic pedicle awl and an alternate embodiment of the present invention constructed with a solenoid winding for directing a magnetic field.

Referring to FIG. 18, a plot of the magnetic field generated by the alternative embodiment of FIGS. 17a and 17b is shown. It can be seen that the magnetic field density is larger on the side of the awl opposite return windings 1856. Return windings 1856 in conjunction with the complete windings 1860 provide for directional projection of the magnetic field.

The embodiments of the present invention are typically applied to the lumbar area of the spine in practice, but may be also applied to the cervical and thoracic spine.

Referring again to FIGS. 5 and 6, the method of use of the electromagnetic pedicle awl is described. In use, an EMG detector 240 is suitably attached to a patient (not shown) with electrodes placed in the muscles of the lower extremity known to respond to specific nerves located outside pedicle wall 222.

FIG. 8 is a pictorial diagram of the muscles 400 of the lower extremity. The nerves for the muscles 400 of the lower extremity are known to be located in the lumbar 2 and sacral 5 regions of spinal column 1. It is effective to place EMG electrodes on muscles 400 and monitor them for electrical impulses brought about by excitation of nerves in the vertebral foramen during pedicle hole placement. In the preferred embodiment of the present invention, electrodes are placed on the vastus lateralis muscle 405, the medial gastrocnemius muscle 406 and tibialis anterior muscle 407. As those skilled in the art can appreciate, many other embodiments of the present invention are realized by utilizing a number of combinations of electrode placement on the muscles 400 of the lower extremity and other places on the human body. As such, the present invention is not limited by the specific location of EMG electrodes: the author simply desires to indicate a preferred placement of EMG electrodes.

Figure 6:
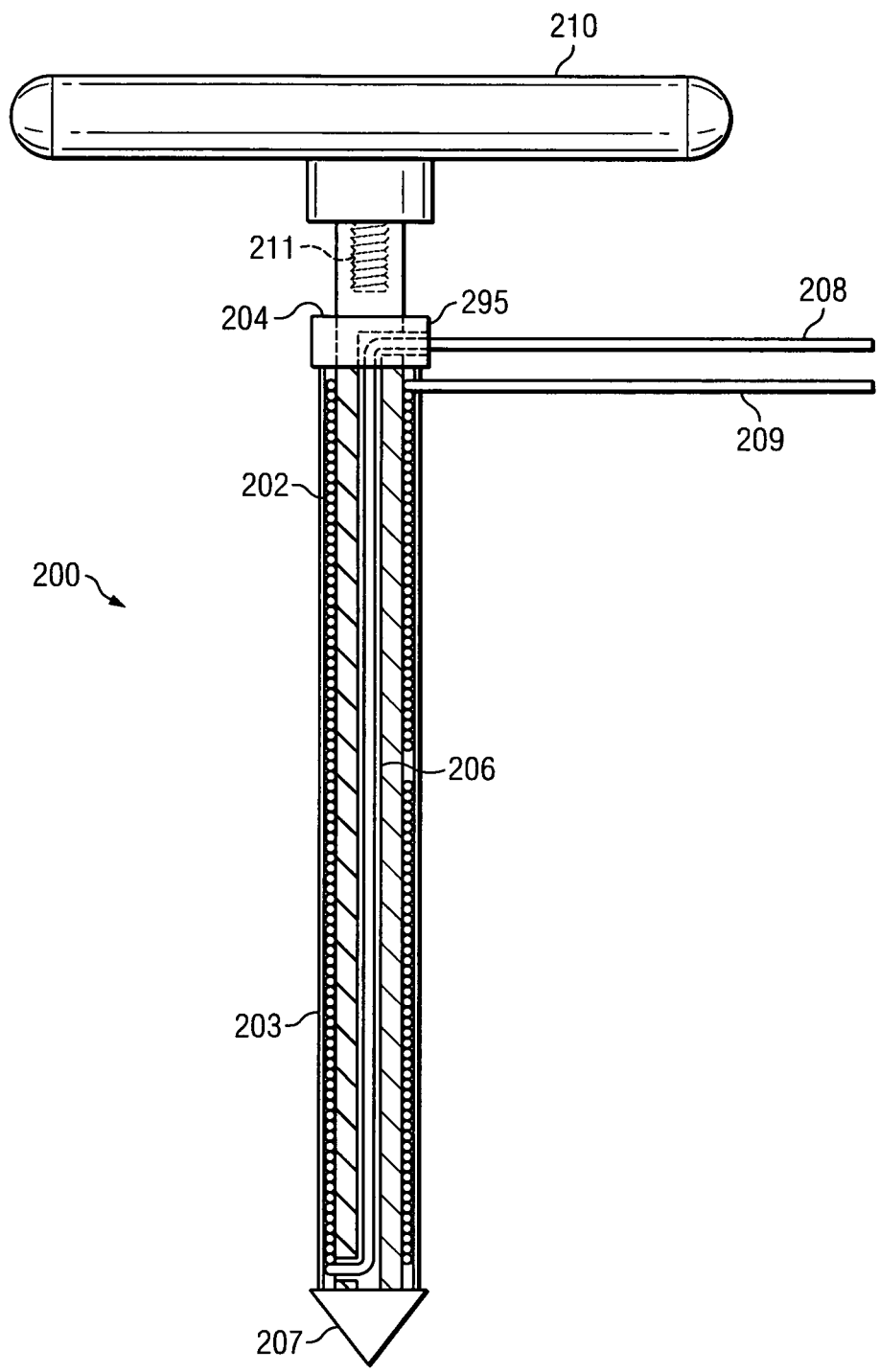
FIG. 6 is a cross-section view of a manual electromagnetic pedicle awl in the preferred embodiment of the present invention.

Referring to FIGS. 5 and 6, electromagnetic pedicle awl 200 is initially positioned by fluoroscopic imaging onto pedicle 220 of vertebra 215 and then rotated using removable handle 210 or lightly impacted with a hammer (not shown) to create a pilot hole through pedicle 220. As electromagnetic pedicle awl 200 is passed through the pedicle 220, EMG detector 240 is monitored for signals that indicate that nerve excitations are resulting from the induced current due to the proximity of the awl tip. In embodiments which include a digital controller for controlling the sweep rate of the electromagnetic field, the sweep rate is set to a predetermined rate. In one preferred embodiment, the predetermined rate varies between one cycle per second and ten cycles per second. In embodiments where a graphical display is provided, the graphical display is monitored for the correlation between the placement of the pedicle awl and response generated by the EMG detector. In response to the EMG detection signals, pedicle awl 200 is redirected to correct placement error.

When used with other surgical techniques, such as in the XLIF procedure, a similar procedure is employed. An EMG detector is suitably attached to the patient with electrodes placed in muscles known to respond to specific nerves within the psoas muscle. The projected entry site of the psoas muscle is exposed and an electromagnetic awl is positioned by intraoperative imaging. A pilot hole is created at the surface of psoas muscle. The EMG detector is monitored as the electromagnetic awl passes through psoas muscle for nerve excitations that result from the flow of ionic current in the nerve due to the localized EMF. If nerve excitations occur, placement corrections can be made to avoid nerve damage.

It should be emphasized that the above-described systems and methods of the present invention, particularly, any exemplary embodiments, are merely possible examples of implementations and are merely set forth for providing a clear understanding of the principles of the invention. The descriptions in this specification are for purposes of illustration only and are not to be construed in a limiting sense. Many variations will be apparent to persons skilled in the art upon reference to the description and may be made to the above-described embodiments of the invention without departing substantially from the spirit and principles of the invention. All such modifications and variations are intended to be included herein within the scope of this disclosure and the present invention and protected by the following claims.

The invention claimed is:

1. A method of creating a hole in a first muscle of the human body utilizing a surgical drilling tool with an integrated time varying magnetic field comprised of:
    bringing the surgical drilling tool in contact with the first muscle;
    manipulating the surgical tool to make the hole;
    connecting an electromyograph to the human body with electrodes placed in a second muscle of the lower extremities of the human body; and
    monitoring the electromyograph for nerve excitation, the nerve excitation arising from interaction of the time varying magnetic field.

2. The method of claim 1 further comprising the steps of:
    creating a graphical map of the location of peripheral nerves to be avoided; and,
    displaying the graphical map.

3. The method of claim 1 further comprising the step of positioning the surgical drilling tool by intraoperative imaging.

4. The method of claim 1 comprising the further step of creating a hole in the psoas muscle.

5. The method of claim 1 comprising the further step of placing the electrodes on at least one of the group of vastus lateralis muscle, medial gastrocnemius muscle and tibialis anterior muscle.

6. A method of creating a hole in a muscle of a human body utilizing a directionally sensitive surgical drilling tool with a set of conductive coils capable of producing a positionally distinct time varying magnetic field comprised of:
    bringing the surgical drilling tool in contact with a given muscle, the muscle containing nerve fibers;

twisting the drill tip of the drilling tool in a drilling process to cut an opening in the given muscle;
connecting an electromyograph to muscles of the human body; and,
monitoring the electromyograph for a nerve excitation arising from the interaction between the nerve fibers and the positionally distinct time varying magnetic field associated with one or more of the set of conductive coils.

7. The method of claim 6 comprising the further steps of:
partially withdrawing the surgical drilling tool based on a feedback signal from the electromyograph; and,
redirecting the surgical drilling tool along a corrective course.

8. The method of claim 6 further comprising the step of displaying the position of one or more of the set of conductive coils.

9. A method for creating a hole in a psoas muscle of a human body comprising of the steps:
providing a surgical awl having a solid core rod having a first end and a second end, a tapered awl tip attached to the first end, a handle for gripping attached to the second end, and a conductive coil surrounding one end of the solid core rod and integrated into the gripping handle;
providing an electric current source attached to the conductive coil and producing an electrical signal so that a time varying magnetic field is generated in the vicinity of the tapered awl tip;
connecting an electromyograph to the human body;
bringing the surgical awl in contact with the psoas muscle, the psoas muscle having nerve cells;
activating the electric current source;
twisting the tapered awl tip of the surgical awl to cut the psoas muscle;
monitoring the electromyograph for nerve excitation arising from the interaction between the nerve cells and the time varying magnetic field; and,
redirecting the surgical awl based on a result from the electromyograph.

10. The method of claim 9, further comprising the steps of:
providing the handle having an index;
monitoring the index to determine position of the surgical awl with respect to the psoas muscle.

11. The method of claim 9, further comprising the steps of:
providing the surgical awl having the conductive coil having four coils, each of the four coils being cylindrical and arranged within the conductive coil with each axis of the four coils being parallel.

12. The method of claim 9, further comprising the steps of:
providing the surgical awl having the conductive coil having a wire with a set of full windings and a set of return windings adjacent the tapered awl tip.

13. The method of claim 9 further comprising the step of displaying a position of the conductive coil.

14. The method of claim 9 further comprising the step of digitally combining a position of the conductive coil with a signal from the electromyograph.

15. The method of claim 9 further comprising the steps of:
creating a graphical map of a location of peripheral nerves to be avoided; and,
displaying the graphical map.

16. The method of claim 9 further comprising the step of positioning the tapered awl tip by intraoperative imaging.

17. The method of claim 9 wherein the step of connecting the electromyograph to the human body further comprises the step of connecting the electromyograph to at least one of the group of vastus lateralis muscle, medial gastrocnemius muscle and tibialis anterior muscle.

* * * * *